(12) United States Patent
Watanabe et al.

(10) Patent No.: US 7,511,191 B1
(45) Date of Patent: Mar. 31, 2009

(54) RAFFINOSE SYNTHASE GENES AND THEIR USE

(75) Inventors: Eijiro Watanabe, Takarazuka (JP); Kenji Oeda, Kyoto (JP)

(73) Assignee: Sumitomo Chemical Company Ltd., Osaka (JP)

( * ) Notice: Subject to any disclaimer, the term of this patent is extended or adjusted under 35 U.S.C. 154(b) by 0 days.

(21) Appl. No.: 09/301,766

(22) Filed: Apr. 29, 1999

(30) Foreign Application Priority Data

| Apr. 30, 1998 | (JP) | ................................. 10-120550 |
| Apr. 30, 1998 | (JP) | ................................. 10-120551 |
| Dec. 4, 1998 | (JP) | ................................. 10-345590 |
| Dec. 10, 1998 | (JP) | ................................. 10-351246 |

(51) Int. Cl.
*C12N 15/29* (2006.01)
*C12N 15/82* (2006.01)
*C12N 15/52* (2006.01)
*C12N 15/80* (2006.01)
*C12N 15/63* (2006.01)

(52) U.S. Cl. ................. 800/284; 435/252.3; 435/320.1; 435/419; 536/23.2; 536/23.6

(58) Field of Classification Search ................ 536/23.1, 536/23.2, 23.6; 435/69.1, 468, 471, 410, 435/419, 254.11, 252.3, 320.1; 800/278, 800/284, 290
See application file for complete search history.

(56) References Cited

U.S. PATENT DOCUMENTS 5,710,365 A  1/1998  Kerr et al. ................... 800/263
5,773,699 A  6/1998  Kerr et al. ................... 800/284
6,166,292 A * 12/2000  Osumi et al. ................. 800/284

FOREIGN PATENT DOCUMENTS

| EP | 0849359 | 6/1998 |
| JP | 10084973 | 4/1998 |
| WO | WO 0024915 A2 | 5/2000 |

OTHER PUBLICATIONS

Castillo et al. J. Agric. Food. Chem. 1990. vol. 38: 351-355.*
Duggleby, R.G. 1997, Identification of an acetolactate synthase small subunit gene from two eukaryotes. Gene 190:245-249.*
Bowie et al 1990, Science 247:1306-1310.*
Lazar et al 1988, Mol. Cell. Biol. 8:1247-1252.*
Broun et al 1998, Science 282:1315-1317.*
Richmond et al 2000, Plant Physiology 124: 495-498.*
Peterbauer et al 2002, Planta 215:839-846.*
Peterbauer et al 2002, Planta 215: 839-846.*
Peterbauer et al 1999, The Plant Journal 20(5): 509-518.*
Derwent Abstract of WO 98/49273 (Nov. 5, 1998).
Derwent Abstract of JP 10-84983 (Apr. 7, 1998).
Derwent Abstract of WO 98/45448 (Oct. 15, 1998).
Eugenia M. Castillo et al., J. Agric. Food Chem., vol. 38, 1990, (XP-000876820), pp. 351-355.

* cited by examiner

*Primary Examiner*—David H Kruse
(74) *Attorney, Agent, or Firm*—Birch Stewart Kolasch & Birch LLP

(57) ABSTRACT

Raffinose synthase genes coding for proteins capable of producing raffinose by combining a D-galactosyl group through an α(1→6) bond with a hydroxyl group attached to the carbon atom at position 6 of a D-glucose residue in a sucrose molecule were isolated from various plants. These raffinose synthase genes are useful to change the content of raffinose family oligosaccharides in plants.

15 Claims, No Drawings

RAFFINOSE SYNTHASE GENES AND THEIR USE

BACKGROUND OF THE INVENTION

1. Field of Invention

The present invention relates to raffinose synthase genes and their use.

2. Disclosure of the Related Art

Raffinose family oligosaccharides are derivatives of sucrose, which are represented by the general formula: o-α-D-galactopyranosyl-(1→6)$_n$-o-α-D-glucopyranosyl-(1→2)-β-D -fluctofuranoside, and they are called "raffinose" when n is 1, "stachyose" when n is 2, "verbascose" when n is 3, and "ajugose" when n is 4.

It has been known that raffinose family oligosaccharides have an effect of giving good conditions of enterobacterial flora, if present at an appropriate amount in food. Therefore, raffinose family oligosaccharides have already been used as a functional food material for addition to some kinds of food and utilized in the field of specific health food. On the other hand, raffinose family oligosaccharides are neither digested nor absorbed in mammals such as human, but are assimilated and decomposed by enterobacteria to generate gases and to cause meteorism and absorption disorder. Therefore, it has been desired to appropriately regulate the amount of raffinose family oligosaccharides in food and feed.

Raffinose family oligosaccharides are synthesized by the raffinose family oligosaccharide biosynthesis system beginning with sucrose in many plants. This biosynthesis system normally involves a reaction for the sequential addition of galactosyl groups from galactinol through an α(1→6) bond to the hydroxyl group attached to the carbon atom at 6-position of the D-glucose residue in a sucrose molecule. Raffinose synthase is the enzyme concerned in the reaction for producing raffinose by allowing a D-galactosyl group derived from galactinol to form the α(1→6) bond with the hydroxyl group attached to the carbon atom at 6-position of the D-glucose residue in a sucrose molecule in the first step of this biosynthesis system. It has been suggested that this enzyme constitutes a rate-limiting step in the above synthesis system, and therefore this enzyme is quite important in the control of biosynthesis of raffinose family oligosaccharides.

Then, a method for controlling an expression level or activity of raffinose synthase in plants by utilizing a raffinose synthase gene is effective to control a biosynthesis system of raffinose family oligosaccharides in plants to increase or decrease the production of raffinose in plants. Thus, a raffinose synthase gene which can be used in such a method has been desired.

OBJECTS OF THE INVENTION

The main object of the present invention is to provide novel raffinose synthase genes from plants.

This object as well as other objects and advantage of the present invention will become apparent to those skilled in the art from the following description.

DETAILED DESCRIPTION OF THE INVENTION

The gene engineering techniques described below can be carried out, for example, according to methods described in "Molecular Cloning: A Laboratory Manual 2nd edition" (1989), Cold Spring Harbor Laboratory Press, ISBN 0-87969-309-6; "Current Protocols In Molecular Biology" (1987), John Wiley & Sons, Inc. ISBN 0-471-50338-X; "Current Protocols In Protein Science" (1995), John Wiley & Sons, Inc. ISBN 0-471-11184-8.

The genes of the present invention can be obtained from soybean, plants belonging to the families Chenopdiaceae such as beet, etc. and Cruciferae such as mustard, rapeseed, etc. Specific examples of the genes of the present invention include those comprising a nucleotide sequence encoding the amino acid sequence represented by SEQ ID NO: 1, the nucleotide sequence represented by SEQ ID NO: 2, a nucleotide sequence encoding the amino acid sequence represented by SEQ ID NO: 3, the nucleotide sequence represented by SEQ ID NO: 4 or by the 236th to 2584th nucleotides in the nucleotide sequence represented by SEQ ID NO: 4, a nucleotide sequence encoding the amino acid sequence represented by SEQ ID NO: 5, the nucleotide sequence represented by SEQ ID NO: 6 or by the 134th to 2467th nucleotides in the nucleotide sequence represented by SEQ ID NO: 6, a nucleotide sequence encoding the amino acid sequence represented by SEQ ID NO: 7, the nucleotide sequence represented by SEQ ID NO: 8 or by the 1st to 1719 th nucleotides in the nucleotide sequence represented by SEQ ID NO: 8, and the like.

The genes of the present invention can be obtained, for example, by the following method.

That is, the genes of the present invention derived from soybean can be obtained, for example, by the following method.

For example, the gene can be obtained by a hybridization method using a nucleic acid having the nucleotide sequence represented by SEQ ID NO: 2 or its partial nucleotide sequence as a probe to detect a nucleic acid fragment which hybridizes to the probe in DNAs derived from soybean, followed by isolating the detected nucleic acid.

In this method, first, a nucleic acid to be used as the probe is prepared. As such a nucleic acid, for example, there is a nucleic acid composed of an oligonucleotide chemically synthesized by a conventional method on the basis of the nucleotide sequence of SEQ ID NO: 2. Specific example thereof includes a nucleic acid having the 800th to the 899th nucleotides in the nucleotide sequence represented by SEQ ID NO: 2.

Alternatively, the gene of the present invention derived from soybean can be obtained by the following method.

For example, tissue of soybean (*Glycine max*) is frozen in liquid nitrogen and ground physically with a mortar or other means into finely divided tissue debris powder. From the tissue debris powder, RNA is extracted by a conventional method. A commercially available RNA extraction kit can be utilized in the extraction. RNA is recovered from thus-obtained RNA extract by ethanol precipitation. Poly-A tailed RNA is fractionated from thus-recovered RNA by a conventional method. A commercially available oligo-dT column can be utilized in this fractionation. cDNA is synthesized from the poly-A tailed RNA thus obtained by a conventional method. The synthesis can be carried out by using a commercially available cDNA synthesis kit. DNA is amplified by PCR using the above-obtained cDNA as the template and primers designed and synthesized on the basis of the nucleotide sequence of SEQ ID NO: 2. More specifically, as the primers, for example, there are primers 11 (SEQ ID NO: 9) and 12 (SEQ ID NO: 10) shown in List 1 herein after. When PCR is carried out by using these primers and as the template cDNA derived from soybean, the genes of the present invention derived from soybean, e.g., the "raffinose synthase gene having a nucleotide sequence encoding the amino acid sequence of SEQ ID NO: 1" and the "raffinose synthase gene having the nucleotide sequence of SEQ ID No: 2" can be obtained.

The amplified DNA can be cloned according to a conventional method, for example, described in "Molecular Cloning: A Laboratory Manual 2nd edition" (1989), Cold Spring Harbor Laboratory Press; or "Current Protocols In Molecular Biology" (1987), John Wiley & Sons, Inc. ISBN 0-471-

50338-X. Alternatively, cloning can be carried out, for example, by using a commercially available cloning kit such as TA cloning kit (Invitrogen) and a commercially available plasmid vector such as pBluescript II (Stratagene). The nucleotide sequence of the DNA clone can be determined by dideoxy terminating method such as that described by F. Sanger, S, Nicklen, A. R. Coulson, Proceedings of National Academy of Science U.S.A. (1977), 74, pp. 5463-5467. For example, preferably, a commercially available kit such as ABI PRISM Dye Terminator Cycle Sequencing Ready Reaction Kit manufactured by Perkin-Elmer can be used.

List 1

Primer 11 (SEQ ID NO: 9): ccaatctgat catgcttgtg ccgaa 25 mer

Primer 12 (SEQ ID NO: 10): ggaacaaagt tatgcactat tatttaaggt 30 mer

The genes of the present invention derived from a Chenopdiaceae plant such as beet can be obtained by the following method.

For example, tissue of a Chenopdiaceae plant such as beet (*Beta vulgaris*) is frozen in liquid nitrogen and ground physically with a mortar or other means into finely divided tissue debris powder. From this tissue debris powder, RNA is extracted by a conventional method. A commercially available RNA extraction kit can be utilized in the extraction. RNA is recovered from the thus-obtained RNA extract by ethanol precipitation. From the recovered RNA, poly-A tailed RNA is fractionated by a conventional method. A commercially available oligo-dT column can be utilized in this fractionation. cDNA is synthesized from the poly-A tailed RNA thus obtained by a conventional method. The synthesis can be carried out by utilizing a commercially available cDNA synthesis kit. DNA is amplified by PCR using the above-obtained cDNA as the template and primers designed and chemically synthesized on the basis of the nucleotide sequence of SEQ ID NO: 4. More specifically, as the primers, for example, there are primers 21 (SEQ ID NO: 11) and 22 (SEQ ID NO: 12) shown in List 2 herein after. When PCR is carried out by using these primers and as the template cDNA derived from be at, the genes of the present invention derived from beet, e.g., the "raffinose synthase gene having a nucleotide sequence encoding the amino acid sequence of SEQ ID NO: 3," and the "raffinose synthase gene having a nucleotide sequence of SEQ ID No: 4" can be obtained. According to a particular purpose, the PCR primers can also be designed and synthesized on the basis of the nucleotide sequence of SEQ ID NO: 4. For example, in order to amplify the "raffinose synthase gene having the nucleotide sequence represented by the 236th to the 2584th nucleotides in the nucleotide sequence represented by SEQ ID NO: 4", preferably, oligonucleotides having the nucleotide sequences represented by primers 23 (SEQ ID NO: 13) and 24 (SEQ ID NO: 14) in List 2 below are synthesized and used as the primers.

The amplified DNA can be cloned according to a conventional method, for example, described in "Molecular Cloning: A Laboratory Manual 2nd edition" (1989), Cold Spring Harbor Laboratory Press; or "Current Protocols In Molecular Biology" (1987), John Wiley & Sons, Inc. ISBN 0-471-50338-X. Alternatively, cloning can be carried out by using a commercially available cloning kit such as TA cloning kit (Invitrogen) and a commercially available plasmid vector such as pBluescript II (Stratagene). The nucleotide sequence of the DNA clone can be determined, for example, by dideoxy terminating method such as that described by F. Sanger, S, Nicklen, A. R. Coulson, Proceedings of National Academy of Science U.S.A. (1977), 74, pp. 5463-5467. For example, preferably, a commercially available kit such as ABI PRISM Dye Terminator Cycle Sequencing Ready Reaction Kit manufactured by Perkin-Elmer can be used.

List 2

Primer 21 (SEQ ID NO: 11): ctaccaaatt ccacaactta aagttca 27 mer

Primer 22 (SEQ ID NO: 12): ggaataataa gcttcacaca tactgtactc tc 32 mer

Primer 23 (SEQ ID NO: 13): atggctccaa gctttagcaa ggaaaattcc 30 mer

Primer 24 (SEQ ID NO: 14): tcaaaataag tactcaacag tggtaaaacc 30 mer

The genes of the present invention derived from Cruciferae plants such as mustard (*Brassica juncea*) and rapeseed (*Brassica napus*) can be obtained by the following method.

For example, tissue of a Cruciferae plant such as mustard or rapeseed is frozen in liquid nitrogen and ground physically with a mortar or other means into finely divided tissue debris powder. From the tissue debris powder, RNA is extracted by a conventional method. A commercially available RNA extraction kit can be utilized in the extraction. The RNA is recovered from thus-obtained RNA extract by ethanol precipitation. Poly-A tailed RNA is fractionated from the RNA thus recovered by a conventional method. A commercially available oligo-dT column can be utilized in the fractionation. cDNA is synthesized from the poly-A tailed RNA thus obtained by a conventional method. The synthesis can be carried out by using a commercially available cDNA synthesis kit. DNA are amplified by PCR using the above-obtained cDNA as a template and primers designed and chemically synthesized on the basis of the nucleotide sequence of SEQ ID NO: 6. For example, when PCR is carried out by using cDNA derived from mustard (*Brassica juncea*) as the template and primers 33 (SEQ ID NO: 17) and 34 (SEQ ID NO: 18) shown in List 3 herein after, the genes from Cruciferae plants of the present invention, e.g., the "raffinose synthase gene having a nucleotide sequence encoding the amino acid sequence of SEQ ID NO: 5," and the "raffinose synthase gene having the nucleotide sequence represented by the 1st to 2654th nucleotides in the nucleotide sequence represented by SEQ ID NO: 6" can be obtained. According to a particular purpose, the PCR primers can also be designed and synthesized on the basis of the nucleotide sequence of SEQ ID NO: 6. For example, in order to amplify DNA encoding the open reading frame region of the "raffinose synthase gene having a nucleotide sequence encoding a protein having the amino acid sequence of SEQ ID NO: 5", and the "raffinose synthase gene having the nucleotide sequence represented by the 134th to the 2467th nucleotides of SEQ ID NO: 6", preferably, oligonucleotides having the nucleotide sequences represented by primers 35 (SEQ ID NO: 19) and 36 (SEQ ID NO: 20) in List 3 are synthesized and used as the primers.

The amplified DNA can be cloned according to a conventional method, for example, described in "Molecular Cloning: A Laboratory Manual 2nd edition" (1989), Cold Spring Harbor Laboratory Press; or "Current Protocols In Molecular Biology" (1987), John Wiley & Sons, Inc. ISBN 0-471-50338-X. Alternatively, cloning can be carried out, for example, by using a commercially available TA cloning kit (Invitrogen) or a commercially available plasmid vector such as pBluescript II (Stratagene). The nucleotide sequence of the DNA clone can be determined by dideoxy terminating method such as that described by F. Sanger, S, Nicklen, A. R. Coulson, Proceedings of National Academy of Science U.S.A. (1977), 74, pp. 5463-5467. For example, preferably, the commercially available ABI PRISM Dye Terminator Cycle Sequencing Ready Reaction Kit of Perkin-Elmer can be used.

List 3

Primer 31 (SEQ ID NO: 15): ttggaagaga agacgccgcc gggaatcgtc 30 mer

Primer 32 (SEQ ID NO: 16): ttaagccccg gcgagagctc tggccggaca 30 mer

Primer 33 (SEQ ID NO: 17): accaatccaa aatctcatca aataatcgca 30 mer

Primer 34 (SEQ ID NO: 18): aaataatagg ggcagtacaa attacaccac 30 mer

Primer 35 (SEQ ID NO: 19): atggctccaccgagcgtaattaaatccga 29 mer

Primer 36 (SEQ ID NO: 20): ctaaaactca tacttaatag aagacaaacc 30 mer

Then, a nucleic acid having a partial nucleotide sequence of the gene of the present invention (herein after referred to as "the gene fragment") which is obtained by the above-described method is labeled and then used as a probe in a hybridization method. The probe can be hybridized to, for example, DNA derived from soybean, a Chenopdiaceae plant or a Cruciferae plant to detect a nucleic acid having the probe specifically bound thereto, thereby detecting a nucleic acid having the raffinose synthase gene.

As the DNA derived from soybean, a Chenopdiaceae plant such as beet or a Cruciferae plant such as mustard or rapeseed, for example, a cDNA library or a genomic DNA library of these plants can be used. The gene library may also be a commercially available gene library as such or a library constructed according to a conventional library construction method, for example, described in "Molecular Cloning: A Laboratory Manual 2 nd edition" (1989), Cold Spring Harbor Laboratory Press; "Current Protocols In Molecular Biology" (1987), John Wiley & Sons, Inc. ISBN 0-471-50338-X.

As the hybridization method, for example, plaque hybridization or colony hybridization can be employed, and they are selected depending upon the kind of vector used in the construction of a library. More specifically, when the library to be used is constructed with a phage vector, a suitable host microorganism is mixed with the phage of the library under infectious conditions to obtain transformants. The transformant is further mixed with a soft agar medium, and the mixture is plated on an agar medium. Thereafter, the mixture is cultured at 37° C. until a plaque of an appropriate size appears. When the library to be used is constructed with a plasmid vector, the plasmid is introduced into a suitable host microorganism to form transformants. The transformant obtained is diluted to a suitable concentration and the dilution is plated on an agar medium, after which it is cultured at 37° C. until a colony of an appropriate size appears. In either case of the above libraries, a membrane filter is placed on the surface of the agar medium after the above cultivation, so that the phage or transformant is transferred to the membrane. This membrane is denatured with an alkali, followed by neutralization, and for example, when a nylon membrane is used, the membrane is irradiated with ultra violet light, so that DNA of the phage or transformant is fixed on the membrane. This membrane is then subjected to a hybridization method wherein the gene fragment which has a partial nucleotide sequence of the gene of the present invention and labeled by a conventional method (herein after referred to as "the labeled gene fragment") is used as a probe. For this method, reference may be made, for example, to D. M. Glover ed., "DNA cloning, a practical approach" IRL PRESS (1985), ISBN 0-947946-18-7. There are various reagents and temperature conditions to be used in the hybridization. For example, in general, prehybridization is carried out by immersion of the membrane in a prehybridization solution [6×SSC (0.9 M NaCl, 0.09 M citric acid), 0.1 to 1 (w/v) % SDS, 100 µg/ml denatured salmon sperm DNA] and incubation at 65° C. for 1 hour. Then, hybridization is carried out by addition and mixing of the labeled gene fragment thereto and incubating the membrane at 42 to 68° C. for 4 to 16 hours.

In the present invention, the "stringent conditions" are those wherein incubation is carried outs for example, at 65 to 68° C. in the above hybridization.

After hybridization, the membrane is taken out and is washed with 2×SSC containing 0.1 to 1 (w/v) % SDS, further rinsed with 0.2×SSC containing 0.1 to 1 (w/v) % SDS, and then dried. The membrane is analyzed, for example, by autoradiography or other techniques to detect the position of the probe on the membrane, thereby detecting the position on the membrane of a nucleic acid having a nucleotide sequence homologous to that of the probe used. The clone corresponding to the position of the nucleic acid thus detected on the membrane is identified on the original agar medium and the positive clone is selected so that the clone having the nucleic acid can be isolated. The same procedures of detection are repeated to purify the clone having the nucleic acid.

Alternatively, a commercially available kit such as GENE TRAPPER cDNA Positive Section System kit (GibcoBRL) can be used. In this method, first, a single-stranded DNA library is hybridized with the biotinylated gene fragment (i.e., probe), followed by adding streptoavidin-bound magnet beads and mixing. From the mixture, the streptoavidin-bound magnetic beads are collected with a magnet, so that single-stranded DNA having a nucleotide sequence homologous to that of the probe used, which has been bound to these beads through the gene fragment, biotin and streptoavidin, is collected and detected. The single-stranded DNA collected can be converted into a double-strand form by reaction with a suitable DNA polymerase using a suitable oligonucleotide as a primer.

As described above, a nucleic acid containing raffinose synthase gene can obtained by detecting a nucleic acid hybridizable to the gene fragment in DNAs of a gene library derived from soybean, a Chenopdiaceae plant or a Cruciferae plant, purifying a clone having the nucleic acid and isolating phage or plasmid DNA from the clone. By preparing the restriction map or determining the nucleotide sequence of the nucleic acid thus obtained according to a conventional method, the nucleic acid containing the gene of the present invention can be confirmed.

For example, the gene of the present invention from a Chenopdiaceae plant can be confirmed by the following point:

The amino acid encoded by the nucleotide sequence thus determined has 75% or more homology to the amino acid sequence represented by the 103rd to 208th amino acids in the amino acid sequence of SEQ ID NO: 3;

80% or more homology to the amino acid sequence represented by the 255th to 271st amino acids in the amino acid sequence of SEQ ID NO:3;

70% or more homology to the amino acid sequence represented by the 289th to 326th amino acids in the amino acid sequence of SEQ ID NO: 3; or 70% or more homology to the amino acid sequence represented by the 610th to 696th amino acids in the amino acid sequence of SEQ ID NO: 3.

The gene of the present invention from a Cruciferae plant can be confirmed, for example, by the following point:

The amino acid sequence encoded by the nucleotide sequence determined has 75% or more homology to the amino acid sequence represented by the 111th to 213th amino acids in the amino acid sequence of SEQ ID NO: 5;

80% or more homology to the amino acid sequence represented by the 260th to 275th amino acids in the amino acid sequence of SEQ ID NO: 5;

70% or more homology to the amino acid sequence represented by the 293rd to 325th amino acids in the amino acid sequence of SEQ ID NO: 5; or 70% or more homology to the amino acid sequence represented by the 609th to 695th amino acids in the amino acid sequence of SEQ ID NO: 5.

The "homology" used herein means the proportion of the number of amino acids in a region, which are identical to those in a different region to be compared, to the number of the entire amino acids in the former region, upon comparing regions having similarity in two amino acid sequences. In this respect, it is preferred that the region having similarity contains more amino acids. Such homology of amino acid sequences can be evaluated by using a commercially available gene analysis software such as GENETIX (Software Kaihatu K. K.).

Further, according to the same manner as described above, a nucleic acid containing raffinose synthase gene can be detected by hybridization to DNA from the desired organism using the gene fragment as a probe to detect a nucleic acid to which the probe specifically binds (herein after referred to as the detection method of the present invention). The gene fragment used herein can be chemically synthesized according to a conventional method on the basis of the nucleotide sequence represented by SEQ ID NO: 2, 4, 6 or 8. Alternatively, it can be prepared by PCR using as primers oligonucleotides chemically synthesized according to a conventional method on the basis of the nucleotide sequence represented by SEQ ID NO: 2, 4, 6 or 8.

The gene fragment may be a part of the non-translated region of the raffinose synthase gene as well as the open reading frame thereof. For example, an oligonucleotide having the same nucleotide sequence as a part of that of 5'-upstream side such as the 1st to 235th nucleotides in the nucleotide sequence of SEQ ID NO: 4, the 1st to 133rd nucleotides in the nucleotide sequence of SEQ ID NO: 6 and the like, or a part of that of 3'-downstream side such as the 2588th to 2675th nucleotides in the nucleotide sequence of SEQ ID NO: 4, the 2468th to 2676th nucleotides in the nucleotide sequence of SEQ ID NO: 6 and the like.

When PCR is carried out by using the gene fragment as primers, it is possible to amplify a nucleic acid containing raffinose synthase gene from DNA derived from the desired organism (herein after referred to as the amplification method of the present invention).

More specifically, for example, oligonucleotides having the nucleotide sequences of the gene fragment are designed and chemically synthesized according to a conventional method. In general, it is preferred that the number of nucleotides is more from a viewpoint that the specificity of annealing is ensured. It is, however, also preferred that the number of nucleotides is not so many from viewpoints that the primers themselves are liable to have a higher structure giving possible deterioration of the annealing efficiency and that complicated procedures are required in the purification after the synthesis. Normally, oligonucleotides composed of 15 to 50 bases are preferred. In this respect, based on the codon table showing the correspondence of amino acids encoded by codons, a mixture of primers can also be synthesized by using a mixture of plural bases so that a residue at a specified position in a primer is changed to different bases according to the variation of codons which can encode one certain amino acid. Alternatively, for example, a base such as inosine which can form a base pair with plural bases can be used instead of the above mixture of plural bases.

Coding Table

Phe: UUU, UUC

Ser: UCU, UCC, UCA, UCG, AGU, AGC

Tyr: UAU, UAC

Cys: UGU, UGC

Stop: UAA, UAG, UGA

Trp: UGG

Leu: UUA, UUG, CUU, CUC, CUA, CUG

Pro: CCU, CCC, CCA, CCG

His: CAU, CAC

Gln: CAA, CAG

Arg: CGU, CGC, CGA, CGG, AGA, AGG

Ile: AUU, AUC, AUA

Thr: ACU, ACC, ACA, ACG

Asn: AAU, AAC

Lys: AAA, AAG

Met: AUG

Val: GUU, GUC, GUA, GUG

Ala: GCU, GCC, GCA, GCG

Asp: GAU, GAC

Gly: GGU, GGC, GGA, GGG

Glu: GAA, GAG

In the above codon table, each codon is shown as the nucleotide sequence in mRNA and its light hand is the 5'-terminus. U represents uracil base in RNA and corresponds to thymine base in DNA.

An oligonucleotide having the same nucleotide sequence as the coding strand of the double-stranded DNA of the gene of the present invention is called a "sense primer" and that having a nucleotide sequence complementary to the coding strand is called an "antisense primer".

A sense primer having the same nucleotide sequence as that of 5'-upstream side in the coding strand of the gene of the present invention, and an antisense primer having a nucleotide sequence complementary to the nucleotide sequence on the 3'-downstream side in this coding strand are used in combination for PCR reaction, for example, with a gene library, genomic DNA or cDNA as the template to amplify DNA. As the gene library to be used, for example, there are a cDNA library and a genomic library derived from soybean, a Chenopdiaceae plant such as beet or a Cruciferae plant such as mustard or rapeseed, etc. The gene library may also be a library constructed according to a conventional library construction method, for example, described in "Molecular Cloning: A Laboratory Manual 2nd edition" (1989), Cold Spring Harbor Laboratory Press; "Current Protocols In Molecular Biology" (1987), John Wiley & Sons, Inc. ISBN 0-471-50338-X, or a commercially available gene library as such. As the genomic DNA or cDNA, for example, there are those prepared from soybean, a Chenopdiaceae plant such as beet or a Cruciferae plant such as mustard or rapeseed, etc.

For example, PCR is carried out by using the primers 31 (SEQ ID NO: 15) and 32 (SEQ ID NO: 16) in the above List 3 and as the template cDNA derived from mustard to amplify DNA having the nucleotide sequence represented by the 749th to 1215th nucleotides in the nucleotide sequence of SEQ ID NO: 6. Further, PCR is carried out by using the primers and as the template cDNA derived from rapeseed to amplify DNA having the nucleotide sequence represented by the 1st to 467th nucleotides in the nucleotide sequence of SEQ ID NO: 8. The nucleic acid thus amplified can be confirmed by conventional electrophoresis. The nucleic acid can be cloned according a conventional method such as that described in "Molecular Cloning: A Laboratory Manual 2nd edition" (1989), Cold Spring Harbor laboratory Press or "Current Protocols in Molecular Biology" (1987), John Wiley & Sons, Inc., ISBN 0-471-50338-X. For the nucleic acid, its restriction map is prepared or its nucleotide sequence is determined by a conventional method, so that the nucleic acid containing raffinose synthase gene or a part thereof can be identified. When the nucleic acid contains a part of raffinose synthase, PCR can be carried out on the basis of its nucleotide sequence to amplify the nucleic acid containing the 5'-upstream side nucleotide sequence or the 3'-downstream side nucleotide sequence. That is, based on the nucleotide sequence of the above-obtained nucleic acid, an antisense primer is designed and synthesized for amplification of the 5'-upstream side part, and a sense primer is designed and synthesized for amplification of the 3'-downstream side part. The nucleotide sequence of the 5'-upstream side part or 3'-downstream side part of the nucleotide sequence already obtained can be determined by the RACE method using these primers and a commercially available kit such as Marathon Kit of Clontech. The full length raffinose synthase gene can be obtained by synthesizing new primers based on both terminal sequences in the nucleotide sequence thus determined and carrying out PCR again.

The above detection method of the present invention can also be used in the analysis of genotypes of a plant such as soybean, a Chenopdiaceae plant or a Cruciferae plant, etc. More specifically, for example, a genomic DNA derived from soybean, a Chenopdiaceae plant or a Cruciferae plant is prepared according to a conventional method, for example, described in "Cloning and Sequence (Plant Biotechnology Experiment Manual)" complied under the supervision of Itaru Watanabe, edited by Masahiro Sugiura, published by Noson Bunka-sha, Tokyo (1989). The genomic DNA is digested with at least several kinds of restriction enzymes, followed by electrophoresis. The electrophoresed DNA is blotted on a filter according to a conventional method. This filter is subjected to hybridization with a probe prepared from DNA having the gene fragment by a conventional method, and DNA to which the probe hybridizes is detected. The DNAs detected are compared in length between different varieties of a specified plant species. The differences in length make possible the analysis of differences in phenotypic characteristics accompanied with the expression of raffinose family oligosaccharides between these varieties. Furthermore, when the DNAs detected by the above method are compared in length between the gene recombinant plant and the non-gene recombinant plant of the same variety, the former plant can be distinguished from the latter plant by the detection of hybridizing bands greater in number or higher in concentration for the former plant than for the latter plant. This method can be carried out according to the RFLP (restriction fragment length polymorphism) method, for example, described in "Plant PCR Experiment Protocols" complied under the supervision of Ko Shimamoto and Takuji Sasaki, published by Shujun-sha, Tokyo (1995), ISBN 4-87962-144-7, pp. 90-94.

Further, the amplification method of the present invention can be used for an analysis of genes of soybean, a Chenopdiaceae plant or a Cruciferae plant, etc. More specifically, for example, the amplification method of the present invention is carried out by using plant genomic DNA prepared from soybean, a Chenopdiaceae plant or a Cruciferae plant to amplify DNA. The amplified DNA is mixed with a formaldehyde solution, followed by heat denaturing at 85° C. for 5 minutes and then quickly cooling on ice. A sample thereof is subjected to electrophoresis on, for example, 6 (w/v) % polyacrylamide gel containing 0 (v/v) % or 10 (v/v) % of glycerol. For this electrophoresis, a commercially available electrophoresis apparatus such as that for SSCP (Single Strand Conformation Polymorphism) can be used and the electrophoresis can be carried out with maintaining the gel at a constant temperature, for example, at 5° C., 25° C., 37° C., etc. From the electrophoresed gel, DNA is detected, for example, by a method such as silver staining method with a commercially available reagent. From the differences of behavior between the varieties in the electrophoresis of the DNA detected, a mutation in the raffinose synthase gene is detected, and an analysis is carried out for differences caused by the mutation in phenotypic characteristics accompanied with the expression of raffinose family oligosaccharides. This method can be carried out according to the SSCP method, for example, described in "Plant PCR Experiment Protocols" complied under the supervision of Ko Shimamoto and Takuji Sasaki, published by Shujun-sha, Tokyo (1995), ISBN 4-87962-144-7, pp. 141-146.

The analysis of the plant gene from soybean, a Chenopdiaceae plant or a Cruciferae plant by the above detection method or amplification method of the present invention can be used not only for the analysis of differences in phenotypic characteristics accompanied with the expression of raffinose family oligosaccharides, but also, for example, for the selection of clones having the desired characters upon production of a novel variety of soybean, a Chenopdiaceae plant or a Cruciferae plant. Further, it can also be used for identification of a clone thus produced and having the characters derived from a recombinant plant upon producing a plant variety using the recombinant plant.

For expression of the gene of the present invention in cells of a host, preferably, a nucleic acid comprising a nucleic acid fragment which contains the gene of the present invention, and a nucleic acid fragment which has a promoter activity in the host cells and joined to the former nucleic acid fragment (herein after referred to as the expression nucleic acid of the present invention) can be used.

The nucleic acid fragment having promoter activity in the expression nucleic acid of the present invention is not limited to a specific one, so long as it is functionable in a host to be transformed. For example, there are synthetic promoters functionable in *Escherichia coli*, such as *E. coli* lactose operon promoter, *E. coli* tryptophan operon promoter and tac promoter, etc.; yeast alcohol dehydrogenase gene (ADH) promoter, adenovirus major late (Ad.ML) promoter, SV40 early promoter, baculovirus promoter and the like. When the host is a plant, the promoter may include, for example, T-DNA derived constitutive promoters such as nopaline synthase gene (NOS) promoter, octopine synthase gene (OCS) promoter, etc.; plant virus-derived promoters such as cauliflower mosaic virus (CaMV)-derived 19S and 35S promoters; inducible promoters such as phenylalanine ammonia-lyase (PAL) gene promoter, chalcone synthase (CHS) gene promoter, pathogenesis-related protein (PR) gene promoter, etc. Furthermore, vector pSUM-GY1 (see JP-A 06-189777/1994) can also be used, which has a promoter giving specific expression in a specified plant tissue, e.g., a promoter of soybean-derived seed storage protein glycinin gene (JP-A 6-189777).

Furthermore, a nucleic acid fragment having a terminator activity can be joined to the expression nucleic acid of the present invention. In this case, it is generally preferred that the expression nucleic acid of the present invention is constructed so that the nucleic acid fragment having a terminator activity is positioned downstream the raffinose synthase gene. The terminator to be used is not particularly limited, so long as it is functionable in cells of a host to be transformed. For example, when the host is a plant, there are T-DNA derived constitutive terminators such as nopaline synthase gene (NOS) terminator, etc.; plant derived terminators such as terminators of allium virus GV1 or GV2, and the like.

The expression nucleic acid of the present invention can be introduced into a host cell according to a conventional gene engineering technique to obtain a transformant. If necessary, the expression nucleic acid of the present invention can be inserted into a vector having a suitable marker depending upon a particular transformation technique for introduction of the nucleic acid into a host cell.

A vector into which the expression nucleic acid of the present invention is inserted can be introduced into a microorganism according to a conventional method, for example, described in "Molecular Cloning: A Laboratory Manual 2nd edition" (1989), Cold Spring Harbor laboratory Press or "Current Protocols in Molecular Biology" (1987), John Wiley & Sons, Inc., ISBN 0-471-50338-X. The microorganism transformed with the vector can be selected on the basis of a selection marker such as antibiotic resistance, auxotrophy or the like. In case that the gene of the present invention is joined to the downstream of an inducible promoter (e.g., tac promoter) in the translatable form in the selected microorganism (e.g., *E. coli* transformant), a translated product of the gene of the present invention can be expressed under conventional culture and inducible conditions and can be recover as a peptide or a protein.

The raffinose synthase activity of the translated product of the gene of the present invention thus prepared can be measured by, for example, a method described in L. Lehle and W. Tanner, Eur. J. Biochem., 38, 103-110 (1973) to identify the translated product having the "capability of binding D-galactosyl group through $\alpha(1\to6)$ bond to the hydroxyl group attached to the carbon atom at 6-position of the D-glucose residue in sucrose molecule". More specifically, for example, the gene of the present invention is cloned in pGEX-4T3 (Pharmacia) to obtain a plasmid containing the expression nucleic acid of the present invention. The resultant plasmid is introduced into, for example, *E. coli* HB101 strain to obtain a transformant. The resultant transformant is culture overnight and 1 ml of the culture is inoculated into 100 ml of LB culture medium. It is incubated at 37° C. for about 3 hours and IPTG (isopropylthio-β-D-galactoside) is added at a final concentration of 1 mM, followed by further incubation for 5 hours. Cells are recovered from the culture broth by centrifugation and are suspended by addition of 10 times of the cell weight of 100 mM Tris-HCl (pH 7.4), 1 mM EDTA, 5 mM DTT (dithiothreitol), 1 mM PMSF (phenylmethylsulfonyl fluoride) and 1 mM benzamide. The suspension is sonicated with a ultrasonic disrupter (Branson) to disrupt the cells. The disrupted cell suspension is centrifuged to recover a soluble protein solution. The resultant protein solution is added to a reaction mixture containing final concentrations of 100 mM Tris-HCl (pH 7.4), 5 mM DTT (dithiothreitol), 0.01% BSA, 200 μM sucrose, 5 mM galactinol and 31.7 μM [$^{14}$C] sucrose. The reaction mixture is incubated at 37° C., followed by addition of 1.5 times in volume of ethanol and stirring. Insoluble materials are remove by centrifugation, the supernatant is spotted on, for example, a HPTLC cellulose thin layer chromatography plate (Merch, HPTLC plates cellulose) and then the plate is developed with n-butanol-pyridine-water-acetic acid (60:40:30:3). The developed plate is dried and analyzed with an imaging analyzer (FUJIX Bio-Image Analyzer BAS-2000II manufactured by Fuji Film) to determine [$^{14}$C] raffinose produced to measure the raffinose synthase activity.

In addition, the translated product as prepared above can also be used as an antigen for producing an antibody. The antibody thus produced can be used for, for example, detection and determination of the gene of the present invention in a crude protein extract prepared from an organism such as a plant.

When the host is a plant, the vector into which the gene of the present invention is inserted can be introduced into plant cells by a conventional means such as *Agrobacterium* infection method (JP-B 2-58917 and JP-A 60-70080), electroporation into protoplasts (JP-A 60-251887 and JP-B 5-68575) or particle gun method (JP-A5-508316 and JP-A63-258525) The plant cell transformed by the introduction of the vector can be selected on the basis of a selection marker, for example, resistance to an antibiotic such as kanamycin or hygromycin. From the plant cell thus transformed, a transformed plant can be regenerated by a conventional plant cell cultivation method, for example, described in "Plant Gene Manipulation Manual (How to Produce Transgenic Plants)" written by Uchimiya, 1990, Kodan-sha Scientific (ISBN 4-06-153513-7), pp. 27-55. Furthermore, the collection of seeds from the transformed plant also makes it possible to prolify the transformed plant. In addition, crossing between the transformed plant obtained and the non-transformed plant makes it possible to produce progenic plants with the characters of the transformed plant.

As gene engineering techniques in soybean, basically, the above general techniques can be employed. More specifically, "transformation of soybean plant strain by particle gun" described in EP 301749, gene introduction methods. for example, described in Torisky, R. S., Kovacs, L., Avdiushko, S., Newman, J. D., Hunt, A. G. and Collins, G. B., "Development of a binary vector system for plant transformation based on the super virulent *Agrobacterium tumefaciens* strain Chry5", Plant Cell Rep., (1997), 17, p. 102-108, etc. can be employed.

As gene engineering techniques in a Chenopdiaceae plant, basically, the above general techniques can be employed. More specifically, gene introduction methods, for example, described in M. Mannerlof, S. Tuvesson, P. Steen and P. Tenning, "Transgenic sugar beet tolerant to glyphosate", Euphytica (1997), 94, p 83-91, B. K. Konwar, "*Agrobacterium tumefacience*-Mediated Genetic Transformation of Sugar Beet (*Beta vulgaris* L.)", J. Plant Biochemistry & Biotechnology (1994), 3, p. 37-41 can be employed.

As gene engineering techniques in a Cruciferae plant, basically, the above general techniques can be employed. More specifically, the gene introduction can be carried out according to a method, for example, described in J. Fry, A. Barnason and R. B. Horsch, "Transformation of *Brassica napus* with *Agrobacterium tumefaciens* based vectors", Plant Cell Reports (1987), 6, 321-325.

For example, when gene introduction is carried out by *Agrobacterium* infection method, first, the above-described expression nucleic acid of the present invention is inserted into a binary vector. The resultant vector can be introduced into, for example, *Agrobacterium tumefaciens* LBA 4404 strain which has been converted into a competent state by treatment with calcium chloride. A transformant can be selected by an appropriate selection method according to the selection marker gene of the vector, for example, cultivation of a strain containing the vector in a culture medium containing an antibiotic in case that the selection marker gene is that giving resistance to the antibiotic such as kanamycin. The resultant transformed *Agrobacterium* strain can be culture in a liquid culture medium, for example, LB medium.

Soybean, a Chenopdiaceae plant or a Cruciferae plant can be transformed by using thus obtained *Agrobacterium* transformant culture broth as described below. For example, seeds from soybean, beet, rapeseed or mustard is sowed aseptically in, for example, ½ MS medium containing 2% sucrose and 0.7% agar. After about 1 week, cotyledons and petioles of the germinated plant are cut off with a scalpel aseptically and transplanted in, for example, MS medium containing 3% sucrose, 0.7% agar, 4.5 µM BA, 0.05 µM 2,4-D and 3.3 µM $AgNO_3$ and cultured for one day. The cotyledons and petioles thus precultured are transferred to 1000-fold dilution of the above *Agrobacterium* culture broth and allowed to stand for 5 minutes. The cotyledons and petioles are transferred to the same medium as that of the preculture again and cultured for about 3 to 4 days. The cotyledones and petioles thus cultured are transferred to, for example, MS medium containing 3% sucrose, 4.5 µM BA, 0.05 µM 2,4-D, 3.3 µM $AgNO_3$ and 500 mg/liter cefotaxim, followed by shaking for 1 day to remove microbial cells. The resultant cotyledons and petioles are transferred to, for example, MS medium containing 3% sucrose, 0.7% agar, 4.5 µM BA, 0.05 µM 2,4-D, 3.3 µM $AgNO_3$ 100 mg/liter cefotaxim and 20 mg/liter kanamycin, followed by culturing for 3 to 4 weeks. Then, the cotyledons and petioles are transferred to, for example, MS medium containing 3% sucrose, 0.7% agar, 4.5 µM BA, 0.05 µM 2,4-D, 100 mg/liter cefotaxim and 20 mg/liter kanamycin and cultured. Culture in this medium is continued with subculturing every 3 to 4 weeks. When a shoot are regenerated, it is subcultured in, for example, MS medium containing 3% sucrose, 0.7% agar and 20 mg/liter kanamycin for 3 to 4 weeks. When the plant makes roots, it is transferred to vermiculite-peat moss (1:1) and acclimatized by culturing at 21 to 22° C. under day and night conditions of 12 hours: 12 hours=day time:night. As the plant grows, it is transferred to appropriate cultivation soil to culture the plant. A genomic DNA is extracted from the leaf of the regenerated plant according to the above method and PCR is carried out by using as primers having partial nucleotide sequences of the expression nucleic acid of the present invention to confirm the insertion of the gene of the present invention into the plant.

As described herein above, by introducing the gene of the present invention into a plant, for example, soybean, a Chenopdiaceae plant or a Cruciferae plant, it is possible to vary the expression level and activity of raffinose synthase in the plant to control the amount of raffinose family oligosaccharides in the plant. The gene of the present invention is useful in techniques for varying the expression level and activity of raffinose synthase in soybean, a Chenopdiaceae plant or a Cruciferae plant on the basis of gene homology, for example, techniques such as homologous recombination and antisense technique, cosuppression and the like.

The following examples further illustrate the present invention in detail but are not to be construed to limit the scope of the present invention.

EXAMPLE 1

Preparation of cDNA Derived from Soybean

About 2 g of immature seeds of soybean (*Glycine max*) Williams 82 were frozen in liquid nitrogen and then ground with a mortar, to which 20 ml of Isogen (Nippon Gene) was added, and the mixture was further thoroughly ground. The ground material was transferred into a centrifugation tube, to which 4 ml of chloroform was added, and the mixture was stirred with a vortex mixer and then centrifuged at 6,500×g for 10 minutes at 4° C. The water layer was collected, to which 10 ml of isopropanol was added, and the mixture was stirred and then centrifuged at 6,500×g for 10 minutes at 4° C. The resulting precipitate was washed with 10 ml of 70% ethanol and then dissolved in 1 ml of elution buffer (10 mM Tris-HCl/pH 7.5, 1 mM EDTA, 0.1% SDS). The solution was allowed to stand at 60° C. for 10 minutes and then centrifuged at 10,000×g for 1 minute to remove insoluble matter. To the resulting supernatant was added an equivalent volume of Oligotex-dT30 (Takara), and the mixture was stirred and then allowed to stand at 65° C. for 5 minutes. Further, the mixture was placed on ice and allowed to stand for 3 minutes, to which 200 µl of 5 M NaCl was added, and the mixture was mixed and then allowed to stand at 37° C. for 10 minutes. The mixture was then centrifuged at 10,000×g for 3 minutes at 4° C. The precipitate was collected and then suspended in 1 ml of TE buffer, and the suspension was allowed to stand at 65° C. for 5 minutes. Further, the suspension was placed on ice and then allowing to stand for 3 minutes, followed by centrifugation at 10,000×g for 3 minutes at 4° C. to remove precipitate.

To the resulting supernatant were added 100 µl of 3M sodium acetate and 2 ml of ethanol to precipitate and collect RNA. The collected RNA was washed twice with 70% ethanol and then dissolved in 20 µl of sterilized water, which was used for the subsequent cDNA synthesis. The amount of RNA obtained was determined by the measurement of absorbance at 260 nm.

For the cDNA synthesis, First Strand Synthesis Kit for RT-PCR (Amersham) and cDNA Synthesis Kit (Takara) were used, and all operations were made according to the protocol attached to kits.

EXAMPLE 2

Cloning of Raffinose Synthase Gene from Soybean cDNA

PCR was carried out by using the cDNA obtained from immature seeds of soybean (*Glycine max*) Williams82 in Example 1 as a template and the primers designed on the basis of the amino acid sequence of SEQ ID NO: 1, i.e., primers having nucleotide sequences shown in List 4 (SEQ ID NOS: 21 and 22) below to amplify a DNA fragment. The PCR was carried out with Gene Amp PCR Systems 2400 and DNA Thermal Cycler Model 480 of Perkin-Elmer using Advantage KlenTaq cDNA Kit of Clontech. The reaction was carried out by repeating the cycle for maintaining at 94° C. for 1 minute, at 50° C. for 3 minutes and then at 72° C. for 3 minutes 40 times to amplify the DNA fragment. The amplified DNA fragment was cloned with TA cloning kit (Invitrogen), followed by sequence reaction using ABI PRISM Dye Terminator Cycle Sequencing Ready Reaction Kit of Perkin-Elmer and analysis of the nucleotide sequence with a 373S DNA sequencer of ABI. Based on this sequence, primers having nucleotide sequences shown in List 5 below were synthesized. The synthesis of cDNA was carried out with Marathon Kit of Clontech using mRNA obtained from leaves of soybean Williams82 in Example 1. The cDNA obtained was ligated to an adapter contained in the kit with ligase. These operations were carried out according to the protocol attached to the kit. By using the adapter-ligated cDNA thus prepared, PCR was carried out with the primers shown in List 5 (SEQ ID NO: 23) according to the same manner as the above. The nucleotide sequence in terminal region of the gene was analyzed according to the protocol attached to the Marathon Kit of Clontech. As a result, the nucleotide sequence of SEQ ID NO: 2 was determined.

List 4

4-5-F primer (SEQ ID NO: 21):

cgatggatgg giaaittiat icaiccigai tgggaiatgt t 41 mer 4-6-RV primer (SEQ ID NO: 22):

ggccacatit tiacia(ag)icc iatiggigci aa 32 mer

List 5

5-SC-2 (SEQ ID NO: 23):

tgttactagg cgaaacaaga gtagctctga 30 mer

EXAMPLE 3

Preparation of cDNA Derived from Chenopdiaceae Plant

About 2 g of leaves of beet (*Beta vulgaris*: haming) was frozen in liquid nitrogen and then ground with a mortar, to which 20 ml of Isogen (Nippon Gene) was added, and the mixture was further thoroughly ground. The ground material was transferred into a centrifugation tube, to which 4 ml of chloroform was added, and the mixture was stirred with a vortex mixer and then centrifuged at 6,500×g for 10 minutes at 4° C. The water layer was collected, to which 10 ml of isopropanol was added, and the mixture was stirred and then centrifuged at 6,500×g for 10 minutes at 4° C. The resulting precipitate was washed with 10 ml of 70% ethanol and then dissolved in 180 µl of DEPC-treated sterilized water. The solution was allowed to stand at 55° C. for 5 minutes and 20 µl of 5MNaCl was added thereto. The resulting solution was purified using BIOMAG mRNA PURIFICATION KIT (PerSeptive Biosystems: Catalog No. 8-MB4003K).

To the resulting mRNA solution were added 3M sodium acetate and ethanol, and RNA was precipitated and collected. The collected RNA was washed twice with 70% ethanol and then dissolved in 20 µl of sterilized water, which was used for the subsequent cDNA synthesis. The amount of RNA obtained was determined by the measurement of absorbance at 260 nm.

For the cDNA synthesis, SMART PCR cDNA Synthesis Kit (Clontech) was used, and all operations were made according to the protocol attached to the kit.

EXAMPLE 4

Analysis of Nucleotide Sequence of Raffinose Synthase Gene from Chenopdiaceae Plant Synthetic DNA primers having the nucleotide sequences shown in List 6 (SEQ ID NOS: 24-27) below were synthesized. The PCR method was carried out with Gene Amp PCR Systems 2400 and DNA Thermal Cycler Model 480 of Perkin-Elmer using Advantage KlenTaq cDNA Kit of Clontech. The PCR was carried out with the above primers (SEQ ID NOS: 24-27) and cDNA of beet obtained in the above Example 3 by repeating the cycle for maintaining at 94° C. for 1 minute, at 50° C. for 3 minutes and then at 72° C. for 3 minutes 40 times. As a result, the combinations of primers 6-3-F (SEQ ID NO: 24) and 6-8-RV (SEQ ID NO: 25) and primers 6-10-F (SEQ ID NO: 26) and 6-6-RV (SEQ ID NO: 27) gave an amplification of about 0.3 kb and 0.6 kb bands, respectively. The amplified DNA fragments were cloned with TA cloning kit (Invitrogen), followed by sequence reaction using ABI PRISM Dye Terminator Cycle Sequencing Ready Reaction Kit of Perkin-Elmer and analysis of nucleotide sequence with a 373S DNA sequencer of ABI. Based on the resulting nucleotide sequences, synthetic DNA primers having nucleotide sequences shown in List 7 (SEQ ID NOS: 28-35) below were prepared and PCR was carried out using cDNA obtained from beet in Example 3 in the same manner as above. As a result, DNA having the nucleotide sequence of SEQ ID NO: 4 was finally obtained from cDNA of beet.

List 6

6-3-F (SEQ ID NO: 24):

cgaggiggit gicciccigg ittigtiati atigaigaig gitggca 47 mer 6-8-RV (SEQ ID NO: 25):

at(t/c)tt(a/g)tcia cigcia(a/g) (a/g)tc (t/c)tccatigt 29 mer 6-10-F (SEQ ID NO: 26):

ggiacitait gg(c/t)ticaigg itgicaiatg gticaitg 38 mer 6-6-RV (SEQ ID NO: 27):

ggccacatit tiacia(a/g)icc iatiggigci aa 32 mer

List 7

7-Sb-1 (SEQ ID NO: 28):

atctatttgt catgacgatg atccga 26 mer

7-Sb-2RV (SEQ ID NO: 29):

ggccctcatt cccatattgg gatgatcctc 30 mer

7-Sb-3RV (SEQ ID NO: 30):

aagcatgcca aacatacaca tgctcaacag 30 mer

7-Sb-4RV (SEQ ID NO: 31):

agacccgggg aaagctttgg ggttactact 30 mer

7-Sb-5 (SEQ ID NO: 32):

tggatgggaa actttataca ccctgact 28 mer

7-Sb-6 (SEQ ID NO: 33):

gacatgttcc catctacaca cccttgtg 28 mer

7-Sb-7 (SEQ ID NO: 34):

ccaatttatg ttagtgatgt tgttggcaag 30 mer

7-Sb-8RV (SEQ ID NO: 35):

tcgactccca gggtagaatt gtcatc 26 mer

EXAMPLE 5

Preparation of cDNA Derived from Cruciferae Plant

About 2 g of leaves of mustard (*Brassica juncea*) was frozen in liquid nitrogen and then ground with a mortar, to which 20 ml of Isogen (*Nippon* Gene) was added, and the mixture was further thoroughly ground. The ground material was transferred into a centrifugation tube, to which 4 ml of chloroform was added, and the mixture was stirred with a vortex mixer and then centrifuged at 6,500×g for 10 minutes at 4° C. The water layer was collected, to which 10 ml of isopropanol was added, and the mixture was stirred and then centrifuged at 6,500×g for 10 minutes at 4° C. The resulting precipitate was washed with 10 ml of 70% ethanol and then dissolved in 180 µl of DEPC-treated sterilized water. The solution was allowed to stand at 55° C. for 5 minutes and to which 20 µl of 5 M NaCl was added. The resulting solution was purified using BIOMAG mRNA PURIFICATION KIT (PerSeptive Biosystems: Catalog No. 8-MB4003K).

To the resulting mRNA solution were added 3M sodium acetate and ethanol, and RNA was precipitated and collected. The collected RNA was washed twice with 70% ethanol and then dissolved in 20 µl of sterilized water, which was used for the subsequent cDNA synthesis. The amount of RNA obtained was determined by the measurement of absorbance at 260 nm.

For the cDNA synthesis, SMART PCR cDNA Synthesis Kit (Clontech) was used, and all operations were carried out according to the protocol attached to the kit.

In the same manner as described in the above, mRNA was purified from immature seeds of rapeseed Westar (*Brassica napus*) and cDNA was synthesized.

EXAMPLE 6

Isolation and Nucleotide Sequence Analysis of Raffinose Synthase Gene derived from Cruciferae Plant DNA primers having the nucleotide sequences shown in List 8 (SEQ ID NOS: 36 and 37) below were synthesized. PCR was carried out with Gene Amp PCR Systems 2400 and DNA Thermal Cycler Model 480 of Perkin-Elmer using Advantage KlenTaq cDNA Kit of Clontech. The PCR was carried out with the above primers and cDNA of mustard obtained in Example 5 by repeating the cycle for maintaining at 94° C. for 1 minute, at 50° C. for 3 minutes and then at 72° C. for 3 minutes 40 times. The reaction products were analyzed by agarose gel electrophoresis. As a result, an amplification of about the 1.2 kb bands was detected. The amplified DNA fragment was cloned with TA cloning kit (Invitrogen), followed by sequence reaction using ABI PRISM Dye Terminator Cycle Sequencing Ready Reaction Kit of Perkin-Elmer and nucleotide sequence analysis with a 373S DNA sequencer of ABI. Based on the resulting nucleotide sequence, synthetic primers having the nucleotide sequences shown in List 9 (SEQ ID NOS: 38 and 39) below were prepared and PCR was carried out using cDNAs from mustard (*Brassica juncea*) and rapeseed Westar (*Brassica napus*) obtained in Example 5 according to the same manner as the above. As a result, the nucleotide sequence represented by the 749th to 1215th nucleotides of SEQ ID NO: 6 and by the 1st to 467th nucleotides of SEQ ID NO: 8 were finally determined for cDNA from mustard (*Brassica juncea*) and rapeseed Westar (*Brassica napus*), respectively.

List 8

8-#1 (SEQ ID NO: 36):

cgattiaaig titggtggac iacicaitgg gtigg 35 mer

8-#10RV (SEQ ID NO: 37):

caitgiacca titgicaicc itgia(ag)ccai taigticc 38 mer

List 9

9-primer-1 (SEQ ID NO: 38):

gttagggttc atatgaacac cttcaagctc 30 mer 9-primer-2RV (SEQ ID NO: 39):

caacggcgag atcttgcatc gtcaac 26 mer

EXAMPLE 7

Nucleotide Sequence Analysis of Raffinose Synthase Full-Length Gene Derived from Cruciferae Plant Based on the nucleotide sequences obtained in Example 6, DNA primers having the nucleotide sequences shown in List 10 (SEQ ID NOS: 40-46) below were synthesized. The cDNAs from mustard (*Brassica juncea*) and rapeseed Westar (*Brassica napus*) obtained in the same manner as described in Example 5 were ligated to adapters contained in Marathon Kit of Clontech. By using the adapter-ligated cDNAs thus prepared, PCR was carried out with primers shown in List 10. 10-B-2RV (SEQ ID NO: 40), 10-B-3RV (SEQ ID NO: 41) and 10-B-4RV (SEQ ID NO: 42) primers were used for nucleotide analysis of 5'-termini, and 10-B-1 (SEQ ID NO: 43), 10-B-8 (SEQ ID NO: 44), 10-B-7 (SEQ ID NO: 45) and 10-B-6 (SEQ ID NO: 46) primers were used for nucleotide analysis of 3'-termini. The nucleotide sequences were analyzed according to the protocol attached to the Marathon Kit of clontech. As a result, the nucleotide sequence of SEQ ID NO: 6 and SEQ ID NO: 8 were determined from mustard (*Brassica juncea*) and rapeseed Westar (*Brassica napus*), respectively.

List 10

10-B-2RV (SEQ ID NO: 40):

ggattcgaca caaaccgcca cgtcatcgtc 30 mer

10-B-3RV (SEQ ID NO: 41):

ccacgtgcac cacccgaact tatcgac 27 mer

10-B-4RV (SEQ ID NO: 42):

aacatcgata ccatcggagt catgtccaat 30 mer

10-B-1 (SEQ ID NO: 43):

gttagggttc atatgaacac cttcaagctc 30 mer

10-B-8 (SEQ ID NO: 44):

tctacgtctg gcacgcgctt tgcggctac 29 mer

10-B-7 (SEQ ID NO: 45):

gttgacgtca tccacatatt ggagatgttg t 31 mer

10-B-6 (SEQ ID NO: 46):

gttatcgcta gcatggagca ctgtaatga 29 mer

EXAMPLE 8

Construction of Expression Vectors in Plant for Raffinose Synthase Gene Derived from Cruciferae Plant Based on the nucleotide sequence of raffinose synthase gene from mustard obtained in Example 7, DNA primers having the nucleotide sequences shown in List 11 (SEQ ID NOS: 47 and 48) were prepared. By using cDNA of mustard, PCR was carried out in the same manner as described in Example 6. The amplified DNA fragment was digested with SacI. The DNA fragment thus digested was ligated to the vector pBI121 (−) previously digested with SacI by using Ligation Kit (Takara). Plasmid pBI121 (Clontech) were digested with BamHI and SadI, and ligated to linkers shown in List 12 (SEQ ID NOS: 49 and 50) to prepare the vector pBI121(−). The vector thus obtained was analyzed by a restriction map and PCR using primers having nucleotide sequences shown in List 13 (SEQ ID NOS: 51-53), and confirmed the direction of inserted raffinose synthase gene. The vector whose raffinose synthase gene from mustard was inserted in the expressible direction was designated BjRS-Sac(+)-121 and the one whose raffinose synthase gene from mustard was inserted in the reverse direction was designated BjRS-Sac(−)-121.

List 11

11-SacI-BjN (SEQ ID NO: 47):

aacgagctca atccaaaatc tcatcaaata atcgc 35 mer

11-SacI-BjintRV (SEQ ID NO: 48):

acaatagttg agggcggaag agtag 25 mer
    List 12

12-BamSac-(+)linker (SEQ ID NO: 49):

gatcgagctc gtgtcggatc cagct 25 mer

12-BamSac-(−)linker (SEQ ID NO: 50):

ggatccgaca cgagctc 17 mer
    List 13

13-35S-3 (SEQ ID NO: 51):

cctcctcgga ttccattgcc cagctatctg 30 mer

13-B-2RV (SEQ ID NO: 52):

ggattcgaca caaaccgcca cgtcatcgtc 30 mer

13-B-8 (SEQ ID NO: 53):

tctacgtctg gcacgcgctt tgcggctac 29 mer

EXAMPLE 9

Transformation with Raffinose Synthase Gene Derived from Cruciferae Plant

The vectors BjRS-Sac(+)-121 and BjRS-Sac(−)-121 prepared in Example 8 were used for the transformation of mustard (*Brassica juncia*) by the *Agrobacterium* infection method.

*Agrobacterium tumefacients* (strain LBA4404 having rifampicin and streptomycin resistance) previously converted into a competent state by calcium chloride treatment was transformed independently with two plasmids BjRS-Sac(+)-121 and BjRS-Sac(−)-121 prepared in Example 8. The transformants were selected on LB medium containing 50 μg/ml rifampicin and 25 μg/ml kanamycin by utilizing the kanamycin resistant character conferred by the kanamycin resistant gene (neomycin phosphotransferase, NPTII) of the introduced plasmids.

The transformant *Agrobacterium* obtained (*Agrobacterium tumefaciens* strain LBA4404: rifampicin and streptomycin resistant) was cultured on LB medium containing 50 μg/ml rifampicin and 25 μg/ml kanamycin at 28° C. for a whole day and night, and the culture was used for the transformation of mustard by the method described below.

The seeds of mustard were aseptically sowed on ½ MS medium containing 2% sucrose and 0.7% agar. After one week, cotyledons and petioles of sprouting plants were cut out with a scalpel, and transferred to MS medium containing 3% sucrose, 0.7% agar, 4.5 μM BA, 0.05 μM 2.4-D and 3.3 μM AgNO$_3$, followed by preculture for 1 day. The precultured cotyledons and petioles were transferred in a 1000-fold dilution of the *Agrobacterium* culture broth and allowed to stand for 5 minutes. The cotyledons and petioles were transferred again to the same medium as used in the preculture, and cultured for 3 to 4 days. The cultured cotyledons and petioles were transferred to MS medium containing 3% sucrose, 4.5 μM BA, 0.05 μM 2.4-D, 3.3 μM AgNO$_3$ and 500 mg/l cefotaxim, and shaken for 1 day to remove microbial cells. The cotyledons and petioles thus treated were transferred to MS medium containing 3% sucrose, 0.7% agar, 4.5 μM BA, 0.05 μM 2.4-D, 3.3 μM AgNO$_3$, 100 mg/l cefotaxim and 20 mg/l kanamycin, and cultured for 3 to 4 weeks. The cotyledons and petioles were transferred to MS medium containing 3% sucrose, 0.7% agar, 4.5 pMBA, 0.05 μM 2.4-D, 100 mg/l cefotaxim and 20 mg/l kanamycin, and cultivated. The cultivation on this medium was continued with subculturing at intervals of 3 to 4 weeks. When shoots are began to regenerate, these shoots are subcultured on MS medium containing 3% sucrose, 0.7% agar and 20 mg/l kanamycin, and cultivated for 3 to 4 weeks. The rooting plants are transferred to vermiculite:peat moss=1:1, and cultivated at 21° C. to 22° C. in a cycle of day/night=12 hours:12 hours. With the progress of plant body growth, the plants are grown with cultivation soil.

BRIEF DESCRIPTION OF SEQUENCES

SEQ ID NO: 1 shows an amino acid sequence of a raffinose synthase protein encoded by the raffinose synthase gene of the present invention.

SEQ ID NO: 2 shows a nucleotide sequence of the raffinose synthase gene of the present invention.

SEQ ID NO: 3 shows an amino acid sequence of a raffinose synthase protein encoded by the raffinose synthase gene obtained from beet.

SEQ ID NO: 4 shows a cDNA nucleotide sequence of the raffinose synthase gene obtained from beet.

SEQ ID NO: 5 shows an amino acid sequence of a raffinose synthase protein encoded by the raffinose synthase gene obtained from mustard.

SEQ ID NO: 6 shows a cDNA nucleotide sequence of the raffinose synthase gene obtained from mustard.

SEQ ID NO: 7 shows an amino acid sequence of a raffinose synthase protein encoded by the raffinose synthase gene obtained from rapeseed.

SEQ ID NO: 8 shows a cDNA nucleotide sequence of the raffinose synthase gene obtained from rapeseed.

List 1

The nucleotide sequences shown in List 1 (SEQ ID NOS: 9 and 10) are examples of the typical primers used in the amplification of a DNA fragment having a raffinose synthase gene. All of these sequences are based on the nucleotide sequence of SEQ ID NO: 2. Primer 11 (SEQ ID NO: 9) is a sense primer and Primer 12 (SEQ ID NO: 10) is an antisense primer. Depending upon the purpose, recognition sequences for suitable restriction enzymes can be added to the 5'-termini of these nucleotide sequences.

List 2

The nucleotide sequences shown in List 2 (SEQ ID NOS: 11-14) are examples of the typical primers used in the amplification of a cDNA of a raffinose synthase gene. Primer 21 (SEQ ID NO: 11) is a sense primer corresponding to the 5'-terminus of the beet-derived raffinose synthase gene. Primer 22 (SEQ ID NO: 12) is an antisense primer corresponding to the 3'-terminus. Depending upon the purpose, recognition sequences for suitable restriction enzymes can be added to the 5'-termini of these nucleotide sequences.

Primer23 (SEQ ID NO: 13) is a sense primer corresponding to the N-terminus of the open reading frame, and primer 24 (SEQ ID NO: 14) is an antisense primer corresponding to the C-terminus.

List 3

Among the nucleotide sequences shown in List 3 (SEQ ID NOS: 15-20), primers 31 (SEQ ID NO: 15) and 32 (SEQ ID NO: 16) are typical primers used in the amplification of a DNA having the partial nucleotide sequence of a raffinose synthase gene. Primer 31 (SEQ ID NO: 15) is a sense primer used in the amplification of a DNA having the partial nucleotide sequence of a raffinose synthase gene from mustard and rapeseed and primer 32 (SEQ ID NO: 16) is an antisense primer. Depending upon the purpose, recognition sequences for suitable restriction enzymes can be added to the 5'-termini of these nucleotide sequences.

Primers 33 (SEQ ID NO: 17) and 34 (SEQ ID NO: 18) are the typical primers used in the amplification of a cDNA of a raffinose synthase gene of mustard. Primers 33 (SEQ ID NO: 17) and 34 (SEQ ID NO: 18) are both based on the nucleotide sequence of raffinose synthase gene in the non-translated region. Primer 33 (SEQ ID NO: 17) is a sense primer corresponding to the 5'-terminal non-translated region of the mustard-derived raffinose synthase gene. Primer 34 (SEQ ID NO: 18) is an antisense primer corresponding to the 3'-terminal non-translated region.

Primers 35 (SEQ ID NO: 19) and 36 (SEQ ID NO: 20) are typical primers used in the amplification of an open reading frame coding for the amino acid sequence of a raffinose synthase protein in the cDNA of a raffinose synthase gene. Primer 35 (SEQ ID NO: 19) is a sense primer corresponding to the 5'-terminus of the above open reading frame. Primer 36 (SEQ ID NO: 20) is an antisense primer corresponding to the 3-terminus. Depending upon the purpose, recognition sequences for suitable restriction enzymes can be added to the 5'-termini of these nucleotide sequences.

List 4

The nucleotide sequences shown in List 4 (SEQ ID NOS: 21 and 22) are of the primers used in the cloning of a DNA fragment having the present raffinose synthase gene. The base represented by the symbol "i" is inosine. The bases shown in parentheses mean that a mixture of those bases is used in the synthesis. The symbol "RV" as used after the primer number means that the primer referred to by this symbol has an antisense sequence.

List 5

The nucleotide sequence shown in List 5 (SEQ ID NO: 23) is of the primer used in the analysis of a nucleotide sequence of the present raffinose synthase gene. 5-SC-2 (SEQ ID NO: 23) is used in the analysis of the present nucleotide sequence in the 3'-terminal region.

List 6

The nucleotide sequences shown in List 6 (SEQ ID NOS: 24-27) are of the primers used in the analysis of the present raffinose synthase gene of beet. The base represented by the symbol "i", is inosine. The bases shown in parentheses mean that a mixture of those bases was used in the synthesis. The symbol "RV" as used after the primer number means that the primer referred to by this symbol has an antisense sequence.

List 7

The nucleotide sequences shown in List 7 (SEQ ID NOS: 28-35) are of the primers synthesized on the partial nucleotide sequences of the beet raffinose synthase gene. The symbol "RV" as used after the primer number means that the primer referred to by this symbol has an antisense sequence.

List 8

The nucleotide sequences shown in List 8 (SEQ ID NOS: 36 and 37) are of the primers used in the analysis of the cDNA nucleotide sequence of a raffinose synthase gene of mustard.

The base represented by the symbol "i" is inosine. The bases shown in parentheses mean that a mixture of those bases. The symbol "RV" as used after the primer number means that the primer referred to by this symbol has an antisense sequence.

List 9

The nucleotide sequences shown in List 9 (SEQ ID NOS: 38 and 39) are of the primers synthesized on the partial nucleotide sequences of the mustard raffinose synthase gene. The symbol "RV" as used after the primer number means that the primer referred to by this symbol has an antisense sequence.

List 10

The nucleotide sequences shown in List 10 (SEQ ID NOS: 40-46) are of the primers used in the analysis of the nucleotide sequences of raffinose synthase gene of mustard and rapeseed. The symbol "RV" as used after the primer number means that the primer referred to by this symbol has an antisense sequence.

List 11

The nucleotide sequences shown in List 11 (SEQ ID NOS: 47 and 48) are of the primers used in the amplification of 5'-terminal region of a mustard raffinose synthase gene. 11-SacI-BjN (SEQ ID NO: 47) is a primer whose SacI restriction site is added to the nucleotide sequence represented by the 4th to 29th nucleotides in SEQ ID NO: 6. 11-SacI-BjintRV (SEQ ID NO: 48) is an antisense primer having a nucleotide sequence corresponding to the nucleotide sequence represented by the 1164th to 1188th nucleotides in SEQ ID NO: 6.

List 12

The nucleotide sequences shown in List 12 (SEQ ID NOS: 49 and 50) are of the adapters added to a mustard cDNA. These synthetic DNA take a double-stranded form when mixed together because they are complementary strands. This adapter has cohesive ends of cleavage sites for the restriction enzymes BamHI and SacI on both termini, and contains the restriction sites for the restriction enzymes BamHI and SacI in the double-stranded region.

List 13

The nucleotide sequences shown in List 13 (SEQ ID NOS: 51-53) are of the primers used in the confirmation of inserting direction of the mustard-derived raffinose synthase gene. 13-35S-3 (SEQ ID NO: 51) is a primer of sense to 35S promoter. 13-B-2RV (SEQ ID NO: 52) is an antisense primer having the nucleotide sequence represented by the 593rd to 622nd nucleotides of SEQ ID NO: 6, 13-B-8 (SEQ ID NO: 53) is a sense primer having the nucleotide sequence represented by the 1110th to 1138th nucleotides in SEQ ID NO: 6.

As described herein above, according to the present invention, it is possible to provide raffinose synthase genes which can be utilized in techniques for varying expression level and activity of raffinose synthase in plants.

Sequence Listing Free Text

SEQ ID NO: 9 to SEQ ID NO: 20: Designed oligonucleotide primer to obtain raffinose synthase gene.

SEQ ID NO: 21 and SEQ ID NO: 22: Designed oligonucleotide primer to obtain raffinose synthase gene, n is i, r is a or SEQ ID NO: 23: Designated oligonucleotide primer to obtain raffinose synthase gene.

SEQ ID NO: 24 to SEQ ID NO: 27: Designed oligonucleotide primer to obtain raffinose synthase gene, n is i, y is t or c, r is a or 9.

SEQ ID NO: 28 to SEQ ID NO: 35: Designed oligonucleotide primer to obtain raffinose synthase gene.

SEQ ID NO: 36 and SEQ ID NO: 37: Designed oligonucleotide primer to obtain raffinose synthase gene, n is i, r is a or g.

SEQ ID NO: 38 to SEQ ID NO: 48: Designed oligonucleotide primer to obtain raffinose synthase gene.

SEQ ID NO: 49 and SEQ ID NO: 50: Designed oligonucleotide linker to obtain raffinose synthase gene.

SEQ ID NO: 51 to SEQ ID NO: 53: Designed oligonucleotide primer to confirm direction of the inserted raffinose synthase gene.

---

What is claimed is:

1. An isolated nucleic acid which comprises a polynucleotide encoding a protein that binds a D-galactosyl group through the α(1→6) bond to the hydroxyl group attached to the carbon atom at 6-position of the D-glucose residue in a sucrose molecule to form raffinose, wherein said polynucleotide comprises a nucleotide sequence selected from the group consisting of:
  (a) a nucleotide sequence encoding the amino acid sequence as depicted in SEQ ID NO: 3,
  (b) a nucleotide sequence depicted by the $236^{th}$ to $2584^{th}$ nucleotides in the nucleotide sequence as depicted in SEQ ID NO: 4,
  (c) a nucleotide sequence encoding the amino acid sequence as depicted in SEQ ID NO: 5, and
  (d) a nucleotide sequence depicted by the $134^{th}$ to $2467^{th}$ nucleotides in the nucleotide sequence as depicted in SEQ ID NO: 6.

2. An isolated nucleic acid comprising a nucleotide sequence encoding the amino acid sequence as depicted in SEQ ID NO: 3.

3. An isolated nucleic acid comprising the nucleotide sequence depicted by the 236th to 2584th nucleotides in the nucleotide sequence as depicted in SEQ ID NO: 4.

4. An isolated nucleic acid comprising a nucleotide sequence encoding the amino acid sequence as depicted in SEQ ID NO: 5.

5. An isolated nucleic acid comprising the nucleotide sequence depicted by the 134th to 2467th nucleotides in the nucleotide sequence as depicted in SEQ ID NO: 6.

6. An isolated nucleic acid comprising the nucleic acid of claim 1, which is operatively linked to a promoter.

7. A vector comprising the nucleic acid of claim 1.

8. A transformant, wherein the nucleic acid of claim 1 is introduced into a host cell.

9. A transformant, wherein the nucleic acid of claim 6 is introduced into a host cell.

10. A transformant, wherein the vector of claim 7 is introduced into a host cell.

11. The transformant of claim 8, wherein the host cell is a microorganism.

12. The transformant of claim 8, wherein the host cell is a plant cell.

13. A method for producing a raffinose synthase which comprises the steps of:
   culturing or growing the transformant of claim 8 to produce the raffinose synthase, and collecting the raffinose synthase.

14. The nucleic acid of claim 6, wherein said promoter is effective in a plant cell.

15. The nucleic acid of claim 6, wherein said promoter is effective in a yeast cell.

* * * * *

UNITED STATES PATENT AND TRADEMARK OFFICE
CERTIFICATE OF CORRECTION

PATENT NO. : 7,511,191 B2
APPLICATION NO. : 09/301766
DATED : March 31, 2009
INVENTOR(S) : Eijiro Watanabe et al.

It is certified that error appears in the above-identified patent and that said Letters Patent is hereby corrected as shown below:

Title page, item (73)

Should read -- Assignee: Sumitomo Chemical Company, Limited, Osaka (JP) --.

Signed and Sealed this

Ninth Day of June, 2009

JOHN DOLL
*Acting Director of the United States Patent and Trademark Office*

SEQUENCE LISTING

<160> NUMBER OF SEQ ID NOS: 53

<210> SEQ ID NO 1
<211> LENGTH: 265
<212> TYPE: PRT
<213> ORGANISM: Glycine max

<400> SEQUENCE: 1

```
Gln Ser Asp His Ala Cys Ala Glu Phe His Ala Ala Ser Arg Ala Ile
                  5                  10                  15

Ser Gly Gly Pro Ile Tyr Val Ser Asp Ser Val Gly Lys His Asn Phe
             20                  25                  30

Lys Leu Leu Lys Lys Leu Val Leu Pro Asp Gly Ser Ile Leu Arg Cys
         35                  40                  45

Gln His Tyr Ala Leu Pro Thr Arg Asp Cys Leu Phe Val Asp Pro Leu
     50                  55                  60

His Asp Gly Lys Thr Met Leu Lys Ile Trp Asn Leu Asn Lys Cys Ser
 65                  70                  75                  80

Gly Val Leu Gly Leu Phe Asn Cys Gln Gly Gly Trp Cys Pro Val
                 85                  90                  95

Thr Arg Arg Asn Lys Ser Ser Ser Asp Tyr Ser His Ser Val Thr Cys
                100                 105                 110

Phe Ala Ser Pro Gln Asp Ile Glu Trp Gly Lys Gly Lys His Pro Val
            115                 120                 125

Cys Ile Lys Gly Val Asp Val Phe Ala Val Tyr Met Phe Lys Asp Asp
        130                 135                 140

Lys Leu Lys Leu Leu Lys Tyr Thr Glu Ser Val Glu Val Ser Leu Glu
145                 150                 155                 160

Pro Phe Ser Cys Glu Leu Leu Thr Val Ser Pro Val Val Ile Leu Pro
                165                 170                 175

Arg Lys Ser Ile Gln Phe Ala Pro Ile Gly Leu Val Asn Met Leu Asn
            180                 185                 190

Ser Gly Gly Ser Ile Met Ser Leu Glu Phe Asp Gln Gln Glu Asn Leu
        195                 200                 205

Ala Arg Ile Gly Val Arg Gly His Gly Glu Met Arg Val Phe Ala Ser
    210                 215                 220

Glu Lys Pro Glu Ser Val Lys Ile Asp Gly Glu Ser Val Glu Phe Asp
225                 230                 235                 240

Tyr Val Asp Arg Thr Val Arg Leu Gln Val Ser Trp Pro Cys Ser Ser
                245                 250                 255

Arg Leu Ser Val Val Glu Tyr Leu Phe
            260                 265
```

<210> SEQ ID NO 2
<211> LENGTH: 928
<212> TYPE: DNA
<213> ORGANISM: Glycine max

<220> FEATURE:
<221> NAME/KEY: CDS
<222> LOCATION: (2)...(799)

<400> SEQUENCE: 2

```
c caa tct gat cat gct tgt gcc gaa ttc cac gct gct tct aga gcc         46
  Gln Ser Asp His Ala Cys Ala Glu Phe His Ala Ala Ser Arg Ala
              5                  10                  15 att tct ggt gga cca att tat gta agc gac tct gtt gga aaa cac aac        94
Ile Ser Gly Gly Pro Ile Tyr Val Ser Asp Ser Val Gly Lys His Asn
         20                  25                  30 ttc aag ttg ctt aag aag ctt gtt cta cct gat ggc tcc att ttg cgg       142
Phe Lys Leu Leu Lys Lys Leu Val Leu Pro Asp Gly Ser Ile Leu Arg
 35                  40                  45 tgt caa cat tat gca ctt ccc acc cga gac tgc tta ttt gta gat cct       190
Cys Gln His Tyr Ala Leu Pro Thr Arg Asp Cys Leu Phe Val Asp Pro
         50                  55                  60 tta cat gat ggg aaa aca atg ctc aaa att tgg aac ctc aat aaa tgt       238
Leu His Asp Gly Lys Thr Met Leu Lys Ile Trp Asn Leu Asn Lys Cys
 65                  70                  75 tcc ggg gtt ttg ggt ctg ttc aat tgc caa gga gga ggt tgg tgc cct       286
Ser Gly Val Leu Gly Leu Phe Asn Cys Gln Gly Gly Gly Trp Cys Pro
 80                  85                  90                  95 gtt act agg cga aac aag agt agc tct gac tat tca cac tcc gtg act       334
Val Thr Arg Arg Asn Lys Ser Ser Ser Asp Tyr Ser His Ser Val Thr
             100                 105                 110 tgc ttt gca agt cct caa gac att gaa tgg ggc aaa ggg aag cac cca       382
Cys Phe Ala Ser Pro Gln Asp Ile Glu Trp Gly Lys Gly Lys His Pro
             115                 120                 125 gtt tgc atc aaa ggg gtg gac gta ttt gct gtg tac atg ttt aag gac       430
Val Cys Ile Lys Gly Val Asp Val Phe Ala Val Tyr Met Phe Lys Asp
             130                 135                 140 gac aag ttg aag ctg ctg aag tac aca gag agt gta gaa gtt tct ctt       478
Asp Lys Leu Lys Leu Leu Lys Tyr Thr Glu Ser Val Glu Val Ser Leu
145                 150                 155 gag cct ttt agt tgt gag ctt ttg acc gtt tct cca gtg gtg atc tta       526
Glu Pro Phe Ser Cys Glu Leu Leu Thr Val Ser Pro Val Val Ile Leu
160                 165                 170                 175 ccc aga aaa tca atc caa ttt gcc cca att gga ttg gta aac atg ctc       574
Pro Arg Lys Ser Ile Gln Phe Ala Pro Ile Gly Leu Val Asn Met Leu
                 180                 185                 190 aac tct ggg ggc tct att atg tca ttg gaa ttt gat caa cag gaa aat       622
Asn Ser Gly Gly Ser Ile Met Ser Leu Glu Phe Asp Gln Gln Glu Asn
             195                 200                 205 ttg gcg agg att ggg gtg aga gga cat ggg gaa atg agg gta ttt gca       670
Leu Ala Arg Ile Gly Val Arg Gly His Gly Glu Met Arg Val Phe Ala
             210                 215                 220 tca gag aag cca gag agt gtc aag att gat gga gaa tct gtg gaa ttt       718
Ser Glu Lys Pro Glu Ser Val Lys Ile Asp Gly Glu Ser Val Glu Phe
225                 230                 235 gat tat gtt gat aga acc gtg agg ctc caa gtc tcg tgg cct tgt tct       766
Asp Tyr Val Asp Arg Thr Val Arg Leu Gln Val Ser Trp Pro Cys Ser
240                 245                 250                 255 tcg agg ttg tcc gta gtc gag tat ttg ttc tga atcatgattt ggtgtccgag    819
Ser Arg Leu Ser Val Val Glu Tyr Leu Phe
                 260                 265 agagccgtgt aatgttcaca taaactgact taagtgcatt aagcaaatcc accttaaata    879
atagtgcata actttgttcc aaaaaaaaaa aaaaaaaaaa aaaaaaaa                 928
```

<210> SEQ ID NO 3
<211> LENGTH: 783
<212> TYPE: PRT
<213> ORGANISM: Beta vulgaris L.

<400> SEQUENCE: 3

Met Ala Pro Ser Phe Ser Lys Glu Asn Ser Lys Thr Cys Asp Glu Val
                 5                   10                  15

Ala Asn His Asp Asp Cys Asn Thr Cys Pro Ile Ile Ser Leu Glu Glu
             20                  25                  30

Ser Asn Phe Met Val Asn Gly His Val Ile Leu Ser Gln Val Pro Ser
         35                  40                  45

Asn Ile Thr Ala Ile Ser Lys Met Gly Phe Asp Gly Leu Phe Val Gly
     50                  55                  60

Phe Asp Ala Pro Glu Pro Lys Ala Arg His Val Val Ser Val Gly Gln
 65                  70                  75                  80

Leu Lys Gly Ile Pro Phe Met Ser Ile Phe Arg Phe Lys Val Trp Trp
                 85                  90                  95

Thr Thr His Trp Thr Gly Ser Asn Gly Arg Asp Leu Glu His Glu Thr
            100                 105                 110

Gln Ile Leu Ile Leu Asp Lys Ser Asp Glu Gly Leu Gly Arg Pro Tyr
        115                 120                 125

Ile Val Ile Leu Pro Leu Ile Glu Gly Pro Phe Arg Ala Ser Leu Gln
    130                 135                 140

Pro Gly Ser Val Asp Asp Tyr Val Asp Ile Cys Val Glu Ser Gly Ser
145                 150                 155                 160

Thr Lys Val Val Gly Asp Ser Phe Arg Ala Val Leu Tyr Ile Arg Ala
                165                 170                 175

Gly Pro Asp Pro Phe Lys Leu Ile Lys Asp Thr Met Lys Glu Val Gln
            180                 185                 190

Ala His Leu Gly Thr Phe Lys Leu Leu Asp Asp Lys Thr Pro Pro Gly
        195                 200                 205

Ile Val Asp Lys Phe Gly Trp Cys Thr Trp Asp Ala Phe Tyr Leu Lys
    210                 215                 220

Val Glu Pro Tyr Gly Val Trp Glu Gly Val Lys Gly Leu Val Glu Asn
225                 230                 235                 240

Gly Val Pro Pro Gly Leu Val Leu Ile Asp Asp Gly Trp Gln Ser Ile
                245                 250                 255

Cys His Asp Asp Pro Ile Thr Asp Gln Glu Gly Ile Asn Arg Thr
            260                 265                 270

Ser Ala Gly Glu Gln Met Pro Cys Arg Leu Ile Lys Tyr Glu Glu Asn
        275                 280                 285

Phe Lys Phe Arg Asp Tyr Lys Ser Pro Asn Ile Met Gly His Glu Asp
    290                 295                 300

His Pro Asn Met Gly Met Arg Ala Phe Val Arg Asp Leu Lys Glu Glu
305                 310                 315                 320

Phe Lys Thr Val Glu His Val Tyr Val Trp His Ala Phe Thr Gly Tyr
                325                 330                 335

Trp Gly Gly Val Arg Pro Asn Val Pro Gly Leu Pro Glu Ala Gln Val
            340                 345                 350

Val Thr Pro Lys Leu Ser Pro Gly Leu Glu Met Thr Met Glu Asp Leu
        355                 360                 365

Ala Val Asp Lys Ile Val Asn Asn Gly Ile Gly Leu Val Gln Pro Asp
    370                 375                 380

```
Lys Ala Gln Glu Leu Tyr Glu Gly Leu His Ser His Leu Glu Asn Cys
385                 390                 395                 400

Gly Ile Asp Gly Val Lys Val Asp Val Ile His Leu Leu Glu Met Met
            405                 410                 415

Ala Glu Asp Tyr Gly Gly Arg Val Glu Leu Ala Lys Thr Tyr Tyr Lys
                420                 425                 430

Ala Ile Thr Glu Ser Val Arg Lys His Phe Lys Gly Asn Gly Val Ile
            435                 440                 445

Ala Ser Met Glu Gln Cys Asn Asp Phe Met Leu Leu Gly Thr Glu Thr
        450                 455                 460

Ile Cys Leu Gly Arg Val Gly Asp Phe Trp Pro Thr Asp Pro Ser
465                 470                 475                 480

Gly Asp Ile Asn Gly Thr Tyr Trp Leu Gln Gly Cys His Met Val His
                485                 490                 495

Cys Ala Tyr Asn Ser Leu Trp Met Gly Asn Phe Ile His Pro Asp Trp
                500                 505                 510

Asp Met Phe Gln Ser Thr His Pro Cys Ala Glu Phe His Ala Ala Ser
            515                 520                 525

Arg Ala Ile Ser Gly Gly Pro Ile Tyr Val Ser Asp Val Val Gly Lys
530                 535                 540

His Asn Ile Pro Leu Leu Lys Arg Leu Val Leu Ala Asp Gly Ser Ile
545                 550                 555                 560

Leu Arg Cys Glu Tyr His Ala Leu Pro Thr Lys Asp Cys Leu Phe Val
                565                 570                 575

Asp Pro Leu His Asp Gly Lys Thr Met Leu Lys Ile Trp Asn Leu Asn
            580                 585                 590

Lys Tyr Asn Gly Val Leu Gly Val Phe Asn Cys Gln Gly Gly Trp
        595                 600                 605

Ser Arg Glu Ser Arg Lys Asn Leu Cys Phe Ser Glu Tyr Ser Lys Pro
        610                 615                 620

Ile Ser Cys Lys Thr Ser Pro Lys Asp Val Glu Trp Glu Asn Gly His
625                 630                 635                 640

Lys Pro Phe Pro Ile Lys Gly Val Glu Cys Phe Ala Met Tyr Phe Thr
                645                 650                 655

Lys Glu Lys Lys Leu Ile Leu Ser Gln Leu Ser Asp Thr Ile Glu Ile
            660                 665                 670

Ser Leu Asp Pro Phe Asp Tyr Glu Leu Ile Val Ser Pro Met Thr
        675                 680                 685

Ile Leu Pro Trp Glu Ser Ile Ala Phe Ala Pro Ile Gly Leu Val Asn
690                 695                 700

Met Leu Asn Ala Gly Gly Ala Val Lys Ser Leu Asp Ile Ser Glu Asp
705                 710                 715                 720

Asn Glu Asp Lys Met Val Gln Val Gly Ile Lys Gly Ala Gly Glu Met
                725                 730                 735

Met Val Tyr Ser Ser Glu Lys Pro Lys Ala Cys Arg Val Asn Gly Glu
            740                 745                 750

Asp Met Glu Phe Glu Tyr Glu Glu Ser Met Ile Lys Val Gln Val Thr
        755                 760                 765

Trp Asn His Asn Ser Gly Gly Phe Thr Thr Val Glu Tyr Leu Phe
        770                 775                 780     783

<210> SEQ ID NO 4
<211> LENGTH: 2690
<212> TYPE: DNA
```

<213> ORGANISM: Beta vulgaris L.
<220> FEATURE:
<221> NAME/KEY: CDS
<222> LOCATION: (236)...(2587)

<400> SEQUENCE: 4

```
ctaccaaatt ccacaactta aagttcacct caatctttat tccattttc ctccctaaac      60 ttcattgtta agattttgta attgaattca aattcttaat tctgaatttt gtcattttt     120 ttgtggggat atttataact atcatattat ttgtgtagat cattctacaa aaagagagt     180 gagtttttt agctcttatt tcctaagaaa ttaatagcaa aagttttgca taact atg     238
                                                              Met
```

| | | | | | | | | | | | | | | | | |
|---|---|---|---|---|---|---|---|---|---|---|---|---|---|---|---|---|
| gct | cca | agc | ttt | agc | aag | gaa | aat | tcc | aag | acg | tgt | gat | gag | gtt | gca | 286 |
| Ala | Pro | Ser | Phe | Ser | Lys | Glu | Asn | Ser | Lys | Thr | Cys | Asp | Glu | Val | Ala | |
| | | 5 | | | | | 10 | | | | | 15 | | | | |
| aac | cat | gat | gat | tgc | aac | acg | tgt | cca | ata | att | tcc | ttg | gaa | gaa | tca | 334 |
| Asn | His | Asp | Asp | Cys | Asn | Thr | Cys | Pro | Ile | Ile | Ser | Leu | Glu | Glu | Ser | |
| | | 20 | | | | | 25 | | | | | 30 | | | | |
| aac | ttc | atg | gtg | aat | ggt | cac | gtg | ata | ttg | tcc | caa | gtt | cca | tcc | aac | 382 |
| Asn | Phe | Met | Val | Asn | Gly | His | Val | Ile | Leu | Ser | Gln | Val | Pro | Ser | Asn | |
| | 35 | | | | | 40 | | | | | 45 | | | | | |
| atc | acg | gcc | att | agt | aaa | atg | ggt | ttt | gat | ggg | ctt | ttt | gtg | ggt | ttt | 430 |
| Ile | Thr | Ala | Ile | Ser | Lys | Met | Gly | Phe | Asp | Gly | Leu | Phe | Val | Gly | Phe | |
| 50 | | | | | 55 | | | | | 60 | | | | | 65 | |
| gat | gct | cca | gag | ccc | aag | gcc | cgg | cac | gtt | gta | tcc | gtg | ggc | cag | ctc | 478 |
| Asp | Ala | Pro | Glu | Pro | Lys | Ala | Arg | His | Val | Val | Ser | Val | Gly | Gln | Leu | |
| | | | 70 | | | | | 75 | | | | | 80 | | | |
| aag | gga | att | ccc | ttc | atg | agt | atc | ttc | agg | ttc | aag | gta | tgg | tgg | act | 526 |
| Lys | Gly | Ile | Pro | Phe | Met | Ser | Ile | Phe | Arg | Phe | Lys | Val | Trp | Trp | Thr | |
| | | | | 85 | | | | | 90 | | | | | 95 | | |
| acc | cat | tgg | act | ggg | tcc | aat | ggg | cgg | gac | ctt | gag | cat | gag | acc | caa | 574 |
| Thr | His | Trp | Thr | Gly | Ser | Asn | Gly | Arg | Asp | Leu | Glu | His | Glu | Thr | Gln | |
| | | | 100 | | | | | 105 | | | | | 110 | | | |
| att | ctc | atc | ctt | gat | aag | tca | gat | gaa | ggt | ttg | ggc | cgt | ccc | tat | att | 622 |
| Ile | Leu | Ile | Leu | Asp | Lys | Ser | Asp | Glu | Gly | Leu | Gly | Arg | Pro | Tyr | Ile | |
| | 115 | | | | | 120 | | | | | 125 | | | | | |
| gtg | atc | ctc | cca | ttg | atc | gaa | ggc | cca | ttt | cgg | gca | tct | ctc | cag | ccg | 670 |
| Val | Ile | Leu | Pro | Leu | Ile | Glu | Gly | Pro | Phe | Arg | Ala | Ser | Leu | Gln | Pro | |
| 130 | | | | | 135 | | | | | 140 | | | | | 145 | |
| ggt | tct | gtt | gat | gac | tat | gtg | gat | ata | tgt | gtt | gag | agt | ggg | tcc | act | 718 |
| Gly | Ser | Val | Asp | Asp | Tyr | Val | Asp | Ile | Cys | Val | Glu | Ser | Gly | Ser | Thr | |
| | | | | 150 | | | | | 155 | | | | | 160 | | |
| aaa | gtt | gtc | gga | gac | tcg | ttc | cgg | gct | gtt | ctt | tat | ata | cgg | gct | ggg | 766 |
| Lys | Val | Val | Gly | Asp | Ser | Phe | Arg | Ala | Val | Leu | Tyr | Ile | Arg | Ala | Gly | |
| | | | 165 | | | | | 170 | | | | | 175 | | | |
| cct | gac | cca | ttt | aag | tta | att | aaa | gat | aca | atg | aag | gaa | gtc | caa | gcc | 814 |
| Pro | Asp | Pro | Phe | Lys | Leu | Ile | Lys | Asp | Thr | Met | Lys | Glu | Val | Gln | Ala | |
| | | 180 | | | | | 185 | | | | | 190 | | | | |
| cat | tta | ggg | act | ttc | aaa | ctc | tta | gat | gac | aaa | act | cct | cca | gga | ata | 862 |
| His | Leu | Gly | Thr | Phe | Lys | Leu | Leu | Asp | Asp | Lys | Thr | Pro | Pro | Gly | Ile | |
| | 195 | | | | | 200 | | | | | 205 | | | | | |
| gtg | gac | aag | ttt | gga | tgg | tgt | aca | tgg | gat | gca | ttt | tac | ctc | aaa | gta | 910 |
| Val | Asp | Lys | Phe | Gly | Trp | Cys | Thr | Trp | Asp | Ala | Phe | Tyr | Leu | Lys | Val | |
| 210 | | | | | 215 | | | | | 220 | | | | | 225 | |
| gag | ccw | tat | ggt | gtt | tgg | gaa | gga | gtt | aaa | gga | ctc | gtc | gaa | aac | ggg | 958 |
| Glu | Pro | Tyr | Gly | Val | Trp | Glu | Gly | Val | Lys | Gly | Leu | Val | Glu | Asn | Gly | |
| | | | | 230 | | | | | 235 | | | | | 240 | | |
| gtc | cca | ccc | ggt | ctc | gta | ctc | att | gat | gat | ggg | tgg | caa | tct | att | tgt | 1006 |
| Val | Pro | Pro | Gly | Leu | Val | Leu | Ile | Asp | Asp | Gly | Trp | Gln | Ser | Ile | Cys | |
| | | | 245 | | | | | 250 | | | | | 255 | | | |

-continued

| | |
|---|---|
| cat gac gat gat ccg att acc gac caa gaa ggg ata aac cgg act tct<br>His Asp Asp Asp Pro Ile Thr Asp Gln Glu Gly Ile Asn Arg Thr Ser<br>260                             265                          270 | 1054 |
| gcc ggc gag caa atg cca tgt aga ttg atc aag tac gag gaa aac ttc<br>Ala Gly Glu Gln Met Pro Cys Arg Leu Ile Lys Tyr Glu Glu Asn Phe<br>275                             280                          285 | 1102 |
| aag ttt agg gac tat aaa agc cca aat att atg ggc cat gag gat cat<br>Lys Phe Arg Asp Tyr Lys Ser Pro Asn Ile Met Gly His Glu Asp His<br>290                             295                          300                          305 | 1150 |
| ccc aat atg gga atg agg gcc ttt gtt agg gac ctt aag gag gag ttc<br>Pro Asn Met Gly Met Arg Ala Phe Val Arg Asp Leu Lys Glu Glu Phe<br>                        310                          315                          320 | 1198 |
| aaa act gtt gag cat gtg tat gtt tgg cat gct ttt acg ggc tat tgg<br>Lys Thr Val Glu His Val Tyr Val Trp His Ala Phe Thr Gly Tyr Trp<br>                       325                          330                          335 | 1246 |
| gga ggg gta agg ccc aat gtt cca ggc cta ccr gag gcc caa gta gta<br>Gly Gly Val Arg Pro Asn Val Pro Gly Leu Pro Glu Ala Gln Val Val<br>                      340                          345                          350 | 1294 |
| acc cca aag ctt tcc ccg ggt ctt gag atg aca atg gaa gat cta gct<br>Thr Pro Lys Leu Ser Pro Gly Leu Glu Met Thr Met Glu Asp Leu Ala<br>355                             360                          365 | 1342 |
| gtg gat aaa att gtt aat aat ggt att ggg ctt gtc cag cct gat aag<br>Val Asp Lys Ile Val Asn Asn Gly Ile Gly Leu Val Gln Pro Asp Lys<br>370                             375                          380                          385 | 1390 |
| gcc caa gaa ctt tat gaa ggg ttg cat tct cat ttg gaa aat tgt ggg<br>Ala Gln Glu Leu Tyr Glu Gly Leu His Ser His Leu Glu Asn Cys Gly<br>                       390                          395                          400 | 1438 |
| att gat gga gtc aaa gtt gat gtc atc cat ttg ttg gag atg atg gca<br>Ile Asp Gly Val Lys Val Asp Val Ile His Leu Leu Glu Met Met Ala<br>                      405                          410                          415 | 1486 |
| gag gac tat gga gga aga gtt gaa cta gca aaa aca tac tat aag gca<br>Glu Asp Tyr Gly Gly Arg Val Glu Leu Ala Lys Thr Tyr Tyr Lys Ala<br>                  420                          425                          430 | 1534 |
| ata aca gaa tca gtg cgt aag cat ttc aaa ggc aac ggt gtg att gct<br>Ile Thr Glu Ser Val Arg Lys His Phe Lys Gly Asn Gly Val Ile Ala<br>435                             440                          445 | 1582 |
| agc atg gag cag tgc aac gat ttc atg ctc ctt ggt act gag acc att<br>Ser Met Glu Gln Cys Asn Asp Phe Met Leu Leu Gly Thr Glu Thr Ile<br>450                             455                          460                          465 | 1630 |
| tgt ctt ggt cgc gtt ggg gat gac ttt tgg cca act gat ccg tct gga<br>Cys Leu Gly Arg Val Gly Asp Asp Phe Trp Pro Thr Asp Pro Ser Gly<br>                      470                          475                          480 | 1678 |
| gat ata aat ggt aca tat tgg ctc caa ggc tgt cat atg gtg cat tgt<br>Asp Ile Asn Gly Thr Tyr Trp Leu Gln Gly Cys His Met Val His Cys<br>                       485                          490 | 1726 |
| gcc tac aat agc tta tgg atg gga aac ttt ata cac cct gac tgg gac<br>Ala Tyr Asn Ser Leu Trp Met Gly Asn Phe Ile His Pro Asp Trp Asp<br>                    500                          505                          510 | 1774 |
| atg ttc caa tct aca cac cct tgt gct gaa ttt cat gct gca tct cgt<br>Met Phe Gln Ser Thr His Pro Cys Ala Glu Phe His Ala Ala Ser Arg<br>515                             520                          525 | 1822 |
| gcg att tct ggt gga cca att tat gtt agt gat gtt gtt ggc aag cat<br>Ala Ile Ser Gly Gly Pro Ile Tyr Val Ser Asp Val Val Gly Lys His<br>530                             535                          540                          545 | 1870 |
| aac atc ccc ttg ctc aaa agg ctc gtc ttg gct gat ggt tcg atc ctt<br>Asn Ile Pro Leu Leu Lys Arg Leu Val Leu Ala Asp Gly Ser Ile Leu<br>                    550                          555                          560 | 1918 |
| cgt tgc gag tac cat gca ctt cct act aag gat tgc cta ttt gta gat<br>Arg Cys Glu Tyr His Ala Leu Pro Thr Lys Asp Cys Leu Phe Val Asp | 1966 |

-continued

```
                  565                 570                 575
cct ttg cac gat ggc aaa aca atg ctc aaa att tgg aac ctc aac aag    2014
Pro Leu His Asp Gly Lys Thr Met Leu Lys Ile Trp Asn Leu Asn Lys
            580                 585                 590 tac aat gga gtg ctt gga gtc ttc aat tgc caa gga gga ggg tgg agc    2062
Tyr Asn Gly Val Leu Gly Val Phe Asn Cys Gln Gly Gly Gly Trp Ser
    595                 600                 605 cgt gag tct cga aaa aat cta tgt ttc tca gag tat tca aaa cct att    2110
Arg Glu Ser Arg Lys Asn Leu Cys Phe Ser Glu Tyr Ser Lys Pro Ile
610                 615                 620                 625 tcc tgc aag aca agt cca aaa gat gtt gaa tgg gag aac gga cac aag    2158
Ser Cys Lys Thr Ser Pro Lys Asp Val Glu Trp Glu Asn Gly His Lys
            630                 635                 640 cca ttc ccc atc aaa gga gtg gaa tgt ttt gcc atg tac ttc acc aag    2206
Pro Phe Pro Ile Lys Gly Val Glu Cys Phe Ala Met Tyr Phe Thr Lys
        645                 650                 655 gaa aaa aag cta atc ctc tca caa cta tct gac acc att gaa ata tca    2254
Glu Lys Lys Leu Ile Leu Ser Gln Leu Ser Asp Thr Ile Glu Ile Ser
    660                 665                 670 ctt gat ccc ttc gat tac gag ctt att gta gtc tct ccg atg aca att    2302
Leu Asp Pro Phe Asp Tyr Glu Leu Ile Val Val Ser Pro Met Thr Ile
675                 680                 685 cta ccc tgg gag tcg atc gca ttt gca ccc ata gga tta gta aac atg    2350
Leu Pro Trp Glu Ser Ile Ala Phe Ala Pro Ile Gly Leu Val Asn Met
690                 695                 700                 705 ctc aac gcc gga ggg gca gtc aag tct ttg gac atc agt gag gat aat    2398
Leu Asn Ala Gly Gly Ala Val Lys Ser Leu Asp Ile Ser Glu Asp Asn
            710                 715                 720 gag gat aag atg gtt cag gtt ggt att aaa ggg gcc gga gaa atg atg    2446
Glu Asp Lys Met Val Gln Val Gly Ile Lys Gly Ala Gly Glu Met Met
        725                 730                 735 gtt tat tca tca gaa aag cca aaa gcg tgt aga gtt aat gga gaa gac    2494
Val Tyr Ser Ser Glu Lys Pro Lys Ala Cys Arg Val Asn Gly Glu Asp
    740                 745                 750 atg gag ttt gag tat gaa gag agc atg att aag gtt caa gtt aca tgg    2542
Met Glu Phe Glu Tyr Glu Glu Ser Met Ile Lys Val Gln Val Thr Trp
755                 760                 765 aac cat aac tca ggt ggt ttt acc act gtt gag tac tta ttt tga gcttg  2592
Asn His Asn Ser Gly Gly Phe Thr Thr Val Glu Tyr Leu Phe
770                 775                 780 aagctaatct aagtctttac ttaatgagtg atgtaactga gtagttgact tgagagtaca  2652
gtatgtgtga agcttattat tccaaaaaaa aaaaaaaa                          2690

<210> SEQ ID NO 5
<211> LENGTH: 777
<212> TYPE: PRT
<213> ORGANISM: Brassica juncea

<400> SEQUENCE: 5

Met Ala Pro Pro Ser Val Ile Lys Ser Asp Ala Ala Val Asn Gly Ile
                5                  10                  15

Asp Leu Ser Gly Lys Pro Leu Phe Arg Leu Glu Gly Ser Asp Leu Leu
            20                  25                  30

Ala Asn Gly His Val Val Leu Thr Asp Val Pro Val Asn Val Thr Val
        35                  40                  45

Thr Ala Ser Pro Tyr Leu Ala Asp Lys Asp Gly Glu Pro Val Asp Ala
    50                  55                  60

Ser Ala Gly Ser Phe Ile Gly Phe Asn Leu Asp Gly Glu Pro Arg Ser
```

-continued

```
            65                  70                  75                  80
Arg His Val Ala Ser Ile Gly Lys Leu Arg Asp Ile Arg Phe Met Ser
                    85                  90                  95
Ile Phe Arg Phe Lys Val Trp Trp Thr Thr His Trp Val Gly Ser Lys
                100                 105                 110
Gly Ser Asp Ile Glu Asn Glu Thr Gln Ile Ile Leu Glu Asn Ser
                115                 120                 125
Gly Ser Gly Arg Pro Tyr Val Leu Leu Pro Leu Leu Glu Gly Ser
            130                 135                 140
Phe Arg Ser Ser Phe Gln Pro Gly Glu Asp Asp Val Ala Val Cys
145                 150                 155                 160
Val Glu Ser Gly Ser Thr Gln Val Thr Gly Ser Glu Phe Arg Gln Val
                165                 170                 175
Val Tyr Val His Ala Gly Asp Asp Pro Phe Lys Leu Val Lys Asp Ala
                180                 185                 190
Met Lys Val Val Arg Val His Met Asn Thr Phe Lys Leu Leu Glu Glu
                195                 200                 205
Lys Thr Pro Pro Gly Ile Val Asp Lys Phe Gly Trp Cys Thr Trp Asp
    210                 215                 220
Ala Phe Tyr Leu Thr Val Asn Pro Asp Gly Val His Lys Gly Val Lys
225                 230                 235                 240
Cys Leu Val Asp Gly Gly Cys Pro Pro Gly Leu Val Leu Ile Asp Asp
                245                 250                 255
Gly Trp Gln Ser Ile Gly His Asp Ser Asp Gly Ile Asp Val Glu Gly
            260                 265                 270
Met Ser Cys Thr Val Ala Gly Glu Gln Met Pro Cys Arg Leu Leu Lys
            275                 280                 285
Phe Gln Glu Asn Phe Lys Phe Arg Asp Tyr Val Ser Pro Lys Asp Lys
            290                 295                 300
Asn Glu Val Gly Met Lys Ala Phe Val Arg Asp Leu Lys Glu Glu Phe
305                 310                 315                 320
Ser Thr Val Asp Tyr Ile Tyr Val Trp His Ala Leu Cys Gly Tyr Trp
                325                 330                 335
Gly Gly Leu Arg Pro Gly Ala Pro Thr Leu Pro Pro Ser Thr Ile Val
            340                 345                 350
Arg Pro Glu Leu Ser Pro Gly Leu Lys Leu Thr Met Gln Asp Leu Ala
            355                 360                 365
Val Asp Lys Ile Val Asp Thr Gly Ile Gly Phe Val Ser Pro Asp Met
            370                 375                 380
Ala Asn Glu Phe Tyr Glu Gly Leu His Ser His Leu Gln Asn Val Gly
385                 390                 395                 400
Ile Asp Gly Val Lys Val Asp Val Ile His Ile Leu Glu Met Leu Cys
                405                 410                 415
Glu Lys Tyr Gly Gly Arg Val Asp Leu Ala Lys Ala Tyr Phe Lys Ala
                420                 425                 430
Leu Thr Ser Ser Val Asn Lys His Phe Asp Gly Asn Gly Val Ile Ala
            435                 440                 445
Ser Met Glu His Cys Asn Asp Phe Met Phe Leu Gly Thr Glu Ala Ile
            450                 455                 460
Ser Leu Gly Arg Val Gly Asp Asp Phe Trp Cys Thr Asp Pro Ser Gly
465                 470                 475                 480
Asp Ile Asn Gly Thr Tyr Trp Leu Gln Gly Cys His Met Val His Cys
                485                 490                 495
```

```
Ala Tyr Asn Ser Leu Trp Met Gly Asn Phe Ile Gln Pro Asp Trp Asp
            500                 505                 510

Met Phe Gln Ser Thr His Pro Cys Ala Glu Phe His Ala Ala Ser Arg
            515                 520                 525

Ala Ile Ser Gly Gly Pro Ile Tyr Ile Ser Asp Cys Val Gly Gln His
        530                 535                 540

Asp Phe Asp Leu Leu Lys Arg Leu Val Leu Pro Asp Gly Ser Ile Leu
545                 550                 555                 560

Arg Cys Glu His Tyr Ala Leu Pro Thr Arg Asp Arg Leu Phe Glu Asp
                565                 570                 575

Pro Leu His Asp Gly Lys Thr Met Leu Lys Ile Trp Asn Leu Asn Lys
            580                 585                 590

Tyr Thr Gly Ile Ile Gly Ala Phe Asn Cys Gln Gly Gly Gly Trp Cys
            595                 600                 605

Arg Glu Thr Arg Arg Asn Gln Cys Phe Ser Gln Cys Val Asn Thr Leu
        610                 615                 620

Thr Ala Thr Thr Asn Pro Lys Asp Val Glu Trp Asn Ser Gly Asn Asn
625                 630                 635                 640

Pro Ile Ser Val Glu Asn Val Glu Glu Phe Ala Leu Phe Leu Ser Gln
                645                 650                 655

Ser Lys Lys Leu Val Leu Ser Gly Pro Asn Asp Asp Leu Glu Ile Thr
            660                 665                 670

Leu Glu Pro Phe Lys Phe Glu Leu Ile Thr Val Ser Pro Val Val Thr
            675                 680                 685

Ile Glu Gly Ser Ser Val Gln Phe Ala Pro Ile Gly Leu Val Asn Met
        690                 695                 700

Leu Asn Thr Ser Gly Ala Ile Arg Ser Leu Val Tyr His Glu Glu Ser
705                 710                 715                 720

Val Glu Ile Gly Val Arg Gly Ala Gly Glu Phe Arg Val Tyr Ala Ser
                725                 730                 735

Arg Lys Pro Ala Ser Cys Lys Ile Asp Gly Glu Val Val Glu Phe Gly
            740                 745                 750

Tyr Glu Glu Ser Met Val Met Val Gln Val Pro Trp Ser Ala Pro Glu
        755                 760                 765

Gly Leu Ser Ser Ile Lys Tyr Glu Phe
    770                 775     777

<210> SEQ ID NO 6
<211> LENGTH: 2690
<212> TYPE: DNA
<213> ORGANISM: Brassica juncea
<220> FEATURE:
<221> NAME/KEY: CDS
<222> LOCATION: (134)...(2467)

<400> SEQUENCE: 6
accaatccaa aatctcatca aataatcgca attaggggaa gtttacaaga ttcatcatct    60
ccgttactat ataactacgc tcttcttcct tcgcctaatc caacttaacc taaaaaccac   120
tctatcagcg aaa atg gct cca ccg agc gta att aaa tcc gat gct gca     169
            Met Ala Pro Pro Ser Val Ile Lys Ser Asp Ala Ala
                 1               5                  10 gtc aac ggc att gac ctc tcc gga aag ccg ctt ttc cgg cta gag ggt    217
Val Asn Gly Ile Asp Leu Ser Gly Lys Pro Leu Phe Arg Leu Glu Gly
         15                  20                  25 tcc gat ctc cta gcc aat ggt cac gtt gtc tta acc gat gta ccg gtt    265
```

```
Ser Asp Leu Leu Ala Asn Gly His Val Val Leu Thr Asp Val Pro Val
     30                  35                  40 aac gtg act gtc act gct tca cct tac cta gct gac aaa gac gga gaa      313
Asn Val Thr Val Thr Ala Ser Pro Tyr Leu Ala Asp Lys Asp Gly Glu
 45                  50                  55                  60 ccg gtt gac gcc tcc gct ggt tca ttc atc ggg ttt aat ctc gac ggt      361
Pro Val Asp Ala Ser Ala Gly Ser Phe Ile Gly Phe Asn Leu Asp Gly
                 65                  70                  75 gag cca cga agc cgc cac gtg gcg tcc atc ggt aaa ctc agg gat att      409
Glu Pro Arg Ser Arg His Val Ala Ser Ile Gly Lys Leu Arg Asp Ile
             80                  85                  90 cga ttc atg agc ata ttc cgt ttc aag gtt tgg tgg act act cac tgg      457
Arg Phe Met Ser Ile Phe Arg Phe Lys Val Trp Trp Thr Thr His Trp
         95                 100                 105 gtc ggt tcc aaa gga tcc gac atc gag aac gag acc cag atc atc atc      505
Val Gly Ser Lys Gly Ser Asp Ile Glu Asn Glu Thr Gln Ile Ile Ile
     110                 115                 120 ctc gag aac tcc ggg tcg ggt cgt cct tat gtt ctt ctt ctg ccg ctt      553
Leu Glu Asn Ser Gly Ser Gly Arg Pro Tyr Val Leu Leu Leu Pro Leu
125                 130                 135                 140 ctt gaa ggc tct ttc cgt tca tcc ttt cag cct ggg gaa gac gat gac      601
Leu Glu Gly Ser Phe Arg Ser Ser Phe Gln Pro Gly Glu Asp Asp Asp
                145                 150                 155 gtg gcg gtt tgt gtc gaa tcc ggg tcg acc cag gtg acc ggg tcg gag      649
Val Ala Val Cys Val Glu Ser Gly Ser Thr Gln Val Thr Gly Ser Glu
            160                 165                 170 ttt cgt caa gtt gtg tat gtt cac gcc gga gac gat ccg ttc aag ctc      697
Phe Arg Gln Val Val Tyr Val His Ala Gly Asp Asp Pro Phe Lys Leu
        175                 180                 185 gtg aaa gac gcg atg aag gtg gtt agg gtt cat atg aac acc ttc aag      745
Val Lys Asp Ala Met Lys Val Val Arg Val His Met Asn Thr Phe Lys
    190                 195                 200 ctc ttg gaa gag aag acr ccg ccg gga atc gtc gat aag ttc ggg tgg      793
Leu Leu Glu Glu Lys Thr Pro Pro Gly Ile Val Asp Lys Phe Gly Trp
205                 210                 215                 220 tgc acg tgg gat gcg ttt tat ttg acg gtg aac cct gac gga gtt cat      841
Cys Thr Trp Asp Ala Phe Tyr Leu Thr Val Asn Pro Asp Gly Val His
                225                 230                 235 aag ggt gtt aag tgt ctc gtc gac ggt ggt tgt ccg ccg gga ttg gtc      889
Lys Gly Val Lys Cys Leu Val Asp Gly Gly Cys Pro Pro Gly Leu Val
            240                 245                 250 cta atc gac gac ggt tgg caa tcg att gga cat gac tcc gat ggt atc      937
Leu Ile Asp Asp Gly Trp Gln Ser Ile Gly His Asp Ser Asp Gly Ile
        255                 260                 265 gat gtt gaa ggg atg agt tgt acc gtc gcc ggg gag caa atg cct tgc      985
Asp Val Glu Gly Met Ser Cys Thr Val Ala Gly Glu Gln Met Pro Cys
    270                 275                 280 agg ctt ctg aaa ttt caa gag aac ttc aag ttc aga gac tac gtc tct     1033
Arg Leu Leu Lys Phe Gln Glu Asn Phe Lys Phe Arg Asp Tyr Val Ser
285                 290                 295                 300 ccg aaa gac aaa aac gaa gtc ggg atg aaa gct ttc gtc aga gat ctg     1081
Pro Lys Asp Lys Asn Glu Val Gly Met Lys Ala Phe Val Arg Asp Leu
                305                 310                 315 aaa gaa gaa ttc tcc acc gtt gat tac atc tac gtc tgg cac gcg ctt     1129
Lys Glu Glu Phe Ser Thr Val Asp Tyr Ile Tyr Val Trp His Ala Leu
            320                 325                 330 tgc ggc tac tgg ggt ggt ctt cgt ccc gga gct cct act ctt ccg ccc     1177
Cys Gly Tyr Trp Gly Gly Leu Arg Pro Gly Ala Pro Thr Leu Pro Pro
        335                 340                 345
```

-continued

| | | |
|---|---|---|
| tca act att gtc cgg cca gag ctc tcg ccg ggg ctt aag ttg acg atg<br>Ser Thr Ile Val Arg Pro Glu Leu Ser Pro Gly Leu Lys Leu Thr Met<br>350                                 355                            360 | | 1225 |
| caa gat ctc gcc gtt gat aag att gtc gat acc gga atc gga ttc gtc<br>Gln Asp Leu Ala Val Asp Lys Ile Val Asp Thr Gly Ile Gly Phe Val<br>365                             370                          375                    380 | | 1273 |
| tcg ccg gac atg gcg aat gag ttt tac gaa ggt ctt cac tct cat ctt<br>Ser Pro Asp Met Ala Asn Glu Phe Tyr Glu Gly Leu His Ser His Leu<br>                        385                        390                    395 | | 1321 |
| caa aac gtc ggt att gac ggc gtt aaa gtt gac gtc atc cac ata ttg<br>Gln Asn Val Gly Ile Asp Gly Val Lys Val Asp Val Ile His Ile Leu<br>                    400                        405                    410 | | 1369 |
| gag atg ttg tgc gag aaa tat ggc ggg aga gta gac ttg gct aaa gct<br>Glu Met Leu Cys Glu Lys Tyr Gly Gly Arg Val Asp Leu Ala Lys Ala<br>415                                 420                            425 | | 1417 |
| tac ttc aag gcg tta act tcc tca gtg aat aag cat ttt gac ggt aac<br>Tyr Phe Lys Ala Leu Thr Ser Ser Val Asn Lys His Phe Asp Gly Asn<br>430                                 435                            440 | | 1465 |
| ggc gtt atc gct agc atg gag cac tgt aat gat ttc atg ttc ctt gga<br>Gly Val Ile Ala Ser Met Glu His Cys Asn Asp Phe Met Phe Leu Gly<br>445                                 450                        455                    460 | | 1513 |
| acc gaa gcc atc tct cta ggt cgt gtc ggt gat gac ttt tgg tgc acg<br>Thr Glu Ala Ile Ser Leu Gly Arg Val Gly Asp Asp Phe Trp Cys Thr<br>                              465                        470                    475 | | 1561 |
| gat cca tca ggc gac ata aac ggc aca tat tgg ctg caa gga tgc cac<br>Asp Pro Ser Gly Asp Ile Asn Gly Thr Tyr Trp Leu Gln Gly Cys His<br>                    480                        485                    490 | | 1609 |
| atg gtc cac tgt gcc tac aac agt ctt tgg atg gga aat ttc atc cag<br>Met Val His Cys Ala Tyr Asn Ser Leu Trp Met Gly Asn Phe Ile Gln<br>              495                        500                    505 | | 1657 |
| cct gat tgg gac atg ttt cag tcc aca cat cct tgt gct gag ttc cat<br>Pro Asp Trp Asp Met Phe Gln Ser Thr His Pro Cys Ala Glu Phe His<br>510                                 515                            520 | | 1705 |
| gct gct tct cgt gcc atc tcc ggt ggg ccc att tac atc agc gat tgt<br>Ala Ala Ser Arg Ala Ile Ser Gly Gly Pro Ile Tyr Ile Ser Asp Cys<br>525                                 530                        535                    540 | | 1753 |
| gtg ggc cag cac gat ttc gat ctc ttg aag cga ctc gtc ttg cct gac<br>Val Gly Gln His Asp Phe Asp Leu Leu Lys Arg Leu Val Leu Pro Asp<br>                        545                        550                    555 | | 1801 |
| ggt tcg att ttg agg tgt gag cac tat gca ctc cca act cgt gac cgt<br>Gly Ser Ile Leu Arg Cys Glu His Tyr Ala Leu Pro Thr Arg Asp Arg<br>                    560                        565                    570 | | 1849 |
| ctc ttt gaa gac cct ctt cat gat ggc aaa acc atg ctc aag att tgg<br>Leu Phe Glu Asp Pro Leu His Asp Gly Lys Thr Met Leu Lys Ile Trp<br>              575                        580                    585 | | 1897 |
| aac ttg aac aag tac act gga att att gga gca ttc aac tgc caa gga<br>Asn Leu Asn Lys Tyr Thr Gly Ile Ile Gly Ala Phe Asn Cys Gln Gly<br>590                                 595                            600 | | 1945 |
| gga gga tgg tgc aga gaa acc cga cgc aac caa tgc ttc tcc caa tgc<br>Gly Gly Trp Cys Arg Glu Thr Arg Arg Asn Gln Cys Phe Ser Gln Cys<br>605                                 610                        615                    620 | | 1993 |
| gtt aac acg tta acc gcc aca aca aat cct aag gac gtt gaa tgg aac<br>Val Asn Thr Leu Thr Ala Thr Thr Asn Pro Lys Asp Val Glu Trp Asn<br>                        625                        630                    635 | | 2041 |
| agt ggg aac aac cca atc tcc gtt gaa aac gtt gaa gag ttt gct ttg<br>Ser Gly Asn Asn Pro Ile Ser Val Glu Asn Val Glu Glu Phe Ala Leu<br>                    640                        645                    650 | | 2089 |
| ttc ttg tct cag tct aag aag ctt gtg ttg tct gga cca aac gat gat<br>Phe Leu Ser Gln Ser Lys Lys Leu Val Leu Ser Gly Pro Asn Asp Asp<br>655                                 660                        665 | | 2137 |

```
ctc gag atc act ttg gag cct ttc aag ttt gag cta atc act gtc tca    2185
Leu Glu Ile Thr Leu Glu Pro Phe Lys Phe Glu Leu Ile Thr Val Ser
            670                 675                 680 cca gtt gtc act att gag ggt agt tcg gtt cag ttt gct cca atc gga    2233
Pro Val Val Thr Ile Glu Gly Ser Ser Val Gln Phe Ala Pro Ile Gly
685                 690                 695                 700 ttg gtt aac atg cta aac act agc ggt gca att cga tcc ttg gtg tat    2281
Leu Val Asn Met Leu Asn Thr Ser Gly Ala Ile Arg Ser Leu Val Tyr
                705                 710                 715 cat gag gaa tcc gtt gag att gga gtt cgt ggt gct gga gag ttc agg    2329
His Glu Glu Ser Val Glu Ile Gly Val Arg Gly Ala Gly Glu Phe Arg
            720                 725                 730 gtt tat gca tca agg aaa cct gcg agc tgc aaa att gat ggt gaa gtt    2377
Val Tyr Ala Ser Arg Lys Pro Ala Ser Cys Lys Ile Asp Gly Glu Val
        735                 740                 745 gtt gag ttt gga tac gag gag tca atg gtg atg gtt caa gtg cct tgg    2425
Val Glu Phe Gly Tyr Glu Glu Ser Met Val Met Val Gln Val Pro Trp
    750                 755                 760 tct gca ccc gag ggt ttg tct tct att aag tat gag ttt tag agtttccga  2476
Ser Ala Pro Glu Gly Leu Ser Ser Ile Lys Tyr Glu Phe
765                 770                 775 aggtgcttat ttgtatcctt ctaaactcct taattatgag ctccgtgccg tttcttttc   2536 tatatggttt ctgagagtga acatctaata tttacccact agggtataat tattggcttt  2596
taagtgattt gttttgaac tgtttttagt ggtgtaattt gtactgcccc tattattttt   2656
catatttatt tgtgaaagat aaaaaaaaaa aaaa                              2690

<210> SEQ ID NO 7
<211> LENGTH: 572
<212> TYPE: PRT
<213> ORGANISM: Brassica napus

<400> SEQUENCE: 7

Leu Glu Glu Lys Thr Pro Pro Gly Ile Val Asp Lys Phe Gly Trp Cys
                5                   10                  15

Thr Trp Asp Ala Phe Tyr Leu Thr Val Asn Pro Asp Gly Val His Lys
            20                  25                  30

Gly Val Lys Cys Leu Val Asp Gly Gly Cys Pro Pro Gly Leu Val Leu
        35                  40                  45

Ile Asp Asp Gly Trp Gln Ser Ile Gly His Asp Ser Asp Gly Ile Asp
    50                  55                  60

Val Glu Gly Met Ser Cys Thr Val Ala Gly Glu Gln Met Pro Cys Arg
65                  70                  75                  80

Leu Pro Lys Phe Gln Glu Asn Phe Lys Phe Arg Asp Tyr Val Ser Pro
                85                  90                  95

Lys Asp Lys Asn Glu Val Gly Met Lys Ala Phe Val Arg Asp Leu Lys
            100                 105                 110

Glu Glu Phe Ser Thr Val Asp Tyr Ile Tyr Val Trp His Ala Leu Cys
        115                 120                 125

Gly Tyr Trp Gly Gly Leu Arg Pro Gly Ala Pro Thr Leu Pro Pro Ser
    130                 135                 140

Thr Ile Val Arg Pro Glu Leu Ser Pro Gly Leu Lys Leu Thr Met Gln
145                 150                 155                 160

Asp Leu Ala Val Asp Lys Ile Ile Asp Thr Gly Ile Gly Phe Val Ser
                165                 170                 175

Pro Asp Met Ala Asn Glu Phe Tyr Glu Gly Leu His Ser His Leu Gln
```

-continued

```
                180                 185                 190
Asn Val Gly Ile Asn Gly Val Lys Val Asp Val Ile His Ile Leu Glu
            195                 200                 205
Met Leu Cys Glu Lys Tyr Gly Arg Val Asp Leu Ala Lys Ala Tyr
        210                 215                 220
Phe Lys Ala Leu Thr Ser Val Asn Lys His Phe Asp Gly Asn Ala
225                 230                 235                 240
Val Ile Ala Ser Met Glu His Cys Asn Asp Phe Met Phe Leu Gly Thr
                245                 250                 255
Glu Ala Ile Ser Leu Gly Arg Val Gly Asp Asp Phe Trp Cys Thr Asp
            260                 265                 270
Pro Ser Gly Asp Ile Asn Gly Thr Tyr Trp Leu Gln Gly Cys His Met
        275                 280                 285
Val His Cys Ala Tyr Asn Ser Leu Trp Met Gly Asn Phe Ile Gln Pro
    290                 295                 300
Asp Trp Asp Met Phe Gln Ser Thr His Pro Cys Ala Glu Phe His Ala
305                 310                 315                 320
Ala Ser Arg Ala Ile Ser Gly Gly Pro Ile Tyr Ile Ser Asp Cys Val
                325                 330                 335
Gly Gln His Asp Phe Asp Leu Leu Arg Arg Leu Val Leu Pro Asp Gly
            340                 345                 350
Ser Ile Leu Arg Cys Glu Tyr Tyr Ala Leu Pro Thr Arg Asp Arg Leu
        355                 360                 365
Phe Glu Asp Pro Leu His Asp Gly Lys Thr Met Leu Lys Ile Trp Asn
    370                 375                 380
Leu Asn Lys Tyr Thr Gly Ile Ile Gly Ala Phe Asn Cys Gln Gly Gly
385                 390                 395                 400
Gly Trp Cys Arg Glu Thr Arg Arg Asp Gln Cys Phe Ser Gln Cys Val
                405                 410                 415
Asn Thr Leu Thr Ala Thr Thr Asn Pro Asn Asp Val Glu Trp Asn Ser
            420                 425                 430
Gly Asn Asn Pro Ile Ser Ile Glu Asn Val Glu Glu Phe Ala Leu Phe
        435                 440                 445
Leu Ser Gln Ser Lys Lys Leu Val Leu Ser Gly Gln Asn Asp Asp Leu
    450                 455                 460
Glu Ile Thr Leu Glu Pro Phe Lys Phe Glu Leu Ile Thr Val Ser Pro
465                 470                 475                 480
Val Val Thr Ile Glu Gly Ser Ser Val Gln Phe Ala Pro Ile Gly Leu
                485                 490                 495
Val Asn Met Leu Asn Thr Ser Gly Ala Ile Arg Ser Leu Val Tyr His
            500                 505                 510
Glu Glu Ser Val Glu Ile Gly Val Arg Gly Ala Gly Glu Phe Arg Val
        515                 520                 525
Tyr Ala Ser Lys Lys Pro Val Ser Cys Lys Ile Asp Gly Glu Asp Val
    530                 535                 540
Glu Phe Gly Tyr Glu Glu Ser Met Val Met Val Gln Val Pro Trp Ser
545                 550                 555                 560
Ala Pro Glu Gly Leu Ser Ser Ile Lys Tyr Leu Phe
                565                 570     572
```

<210> SEQ ID NO 8
<211> LENGTH: 1762
<212> TYPE: DNA
<213> ORGANISM: Brassica napus

```
<220> FEATURE:
<221> NAME/KEY: CDS
<222> LOCATION: (1)...(1719)

<400> SEQUENCE: 8 ttg gaa gaa aaa acg ccg ccg gga atc gtc gat aag ttc ggg tgg tgc      48
Leu Glu Glu Lys Thr Pro Pro Gly Ile Val Asp Lys Phe Gly Trp Cys
  1               5                  10                  15 acg tgg gat gcg ttt tat ttg acg gtg aac cct gac gga gtt cat aag      96
Thr Trp Asp Ala Phe Tyr Leu Thr Val Asn Pro Asp Gly Val His Lys
             20                  25                  30 ggt gtt aag tgt ctc gtc gac ggt ggt tgt ccg ccg gga ttg gtc cta     144
Gly Val Lys Cys Leu Val Asp Gly Gly Cys Pro Pro Gly Leu Val Leu
         35                  40                  45 atc gac gac ggt tgg caa tcg att gga cat gac tcc gat ggt atc gat     192
Ile Asp Asp Gly Trp Gln Ser Ile Gly His Asp Ser Asp Gly Ile Asp
     50                  55                  60 gtt gaa ggg atg agt tgt acc gtc gcc ggg gag caa atg cct tgc agg     240
Val Glu Gly Met Ser Cys Thr Val Ala Gly Glu Gln Met Pro Cys Arg
 65                  70                  75                  80 ctt ccg aaa ttt caa gag aac ttc aag ttc aga gac tac gtc tct ccg     288
Leu Pro Lys Phe Gln Glu Asn Phe Lys Phe Arg Asp Tyr Val Ser Pro
                 85                  90                  95 aaa gac aaa aac gaa gtc ggg atg aaa gct ttc gtc aga gat ctg aaa     336
Lys Asp Lys Asn Glu Val Gly Met Lys Ala Phe Val Arg Asp Leu Lys
            100                 105                 110 gaa gaa ttc tcc acc gtt gat tac atc tac gtc tgg cac gcg ctt tgc     384
Glu Glu Phe Ser Thr Val Asp Tyr Ile Tyr Val Trp His Ala Leu Cys
        115                 120                 125 ggy tac tgg ggw ggt ctt cgt ccc gga gct cct act ctt ccg ccs tcr     432
Gly Tyr Trp Gly Gly Leu Arg Pro Gly Ala Pro Thr Leu Pro Pro Ser
    130                 135                 140 act att gtc cgr cca gag ctc tcg ccg ggg ctt aag ttg acg atg caa     480
Thr Ile Val Arg Pro Glu Leu Ser Pro Gly Leu Lys Leu Thr Met Gln
145                 150                 155                 160 gat ctc gcc gtt gat aag atc atc gat acc gga atc gga ttc gtc tcg     528
Asp Leu Ala Val Asp Lys Ile Ile Asp Thr Gly Ile Gly Phe Val Ser
                165                 170                 175 ccg gac atg gcg aac gag ttt tac gaa ggt ctt cac tct cat ctt caa     576
Pro Asp Met Ala Asn Glu Phe Tyr Glu Gly Leu His Ser His Leu Gln
            180                 185                 190 aac gtc ggc att aac ggc gtt aaa gtt gac gtt atc cac ata ctg gag     624
Asn Val Gly Ile Asn Gly Val Lys Val Asp Val Ile His Ile Leu Glu
        195                 200                 205 atg ttg tgc gag aaa tat ggc ggg aga gtt gac ttg gct aaa gct tac     672
Met Leu Cys Glu Lys Tyr Gly Gly Arg Val Asp Leu Ala Lys Ala Tyr
    210                 215                 220 ttc aag gcg tta acg tcg tca gtg aat aag cat ttt gac ggc aac gcc     720
Phe Lys Ala Leu Thr Ser Ser Val Asn Lys His Phe Asp Gly Asn Ala
225                 230                 235                 240 gtt atc gcc agc atg gag cac tgt aat gac ttc atg ttc ctt gga acc     768
Val Ile Ala Ser Met Glu His Cys Asn Asp Phe Met Phe Leu Gly Thr
                245                 250                 255 gaa gcc atc tct cta ggt cgt gtc ggt gat gac ttt tgg tgc acg gat     816
Glu Ala Ile Ser Leu Gly Arg Val Gly Asp Asp Phe Trp Cys Thr Asp
            260                 265                 270 cca tct ggc gac att aac ggc acg tat tgg ctg caa gga tgt cac atg     864
Pro Ser Gly Asp Ile Asn Gly Thr Tyr Trp Leu Gln Gly Cys His Met
        275                 280                 285 gtc cac tgt gcc tac aac agt ctt tgg atg gga aat ttc atc cag cct     912
```

-continued

```
                Val His Cys Ala Tyr Asn Ser Leu Trp Met Gly Asn Phe Ile Gln Pro
                    290                 295                 300 gat tgg gac atg ttt cag tcc aca cat cct tgt gct gag ttc cat gct        960
Asp Trp Asp Met Phe Gln Ser Thr His Pro Cys Ala Glu Phe His Ala
305                 310                 315                 320 gct tca cgt gcc atc tcc ggt ggg ccc att tac atc agc gat tgt gtg       1008
Ala Ser Arg Ala Ile Ser Gly Gly Pro Ile Tyr Ile Ser Asp Cys Val
                325                 330                 335 ggc cag cac gat ttc gat ctc ttg agg aga ctc gtt ttg cct gac ggt       1056
Gly Gln His Asp Phe Asp Leu Leu Arg Arg Leu Val Leu Pro Asp Gly
            340                 345                 350 tcg att ttg agg tgt gag tac tat gct ctc cca act cgt gac cgt ctc       1104
Ser Ile Leu Arg Cys Glu Tyr Tyr Ala Leu Pro Thr Arg Asp Arg Leu
        355                 360                 365 ttt gaa gac cct ctt cat gat ggc aaa acc atg ctc aag att tgg aac       1152
Phe Glu Asp Pro Leu His Asp Gly Lys Thr Met Leu Lys Ile Trp Asn
370                 375                 380 ttg aac aag tac act gga atc atc gga gca ttc aac tgt caa gga gga       1200
Leu Asn Lys Tyr Thr Gly Ile Ile Gly Ala Phe Asn Cys Gln Gly Gly
385                 390                 395                 400 gga tgg tgc aga gaa act cga cgc gac caa tgc ttc tcc caa tgc gtt       1248
Gly Trp Cys Arg Glu Thr Arg Arg Asp Gln Cys Phe Ser Gln Cys Val
                405                 410                 415 aac acg tta acc gcc aca aca aat cct aat gac gtt gaa tgg aac agt       1296
Asn Thr Leu Thr Ala Thr Thr Asn Pro Asn Asp Val Glu Trp Asn Ser
            420                 425                 430 ggg aac aac ccg atc tcc att gaa aac gtt gaa gag ttt gct ttg ttc       1344
Gly Asn Asn Pro Ile Ser Ile Glu Asn Val Glu Glu Phe Ala Leu Phe
        435                 440                 445 ttg tct caa tcc aag aag ctt gtg ttg tcc ggg caa aac gat gat ctc       1392
Leu Ser Gln Ser Lys Lys Leu Val Leu Ser Gly Gln Asn Asp Asp Leu
450                 455                 460 gag atc aca tta gag ccc ttc aag ttc gag ctc atc act gtc tca cca       1440
Glu Ile Thr Leu Glu Pro Phe Lys Phe Glu Leu Ile Thr Val Ser Pro
465                 470                 475                 480 gtt gtc acc att gag ggc agt tcg gtt cag ttt gct cca atc gga ttg       1488
Val Val Thr Ile Glu Gly Ser Ser Val Gln Phe Ala Pro Ile Gly Leu
                485                 490                 495 gtt aac atg ctt aac act agc ggt gcg att cga tcc ttg gtt tat cat       1536
Val Asn Met Leu Asn Thr Ser Gly Ala Ile Arg Ser Leu Val Tyr His
            500                 505                 510 gag gaa tcc gtt gag atc ggt gtt cgt ggt gct gga gaa ttc agg gtt       1584
Glu Glu Ser Val Glu Ile Gly Val Arg Gly Ala Gly Glu Phe Arg Val
        515                 520                 525 tat gca tcg aag aaa cct gtg agc tgc aag att gat ggt gaa gat gtt       1632
Tyr Ala Ser Lys Lys Pro Val Ser Cys Lys Ile Asp Gly Glu Asp Val
530                 535                 540 gag ttt ggg tac gaa gag tca atg gtg atg gtt caa gtg cct tgg tct       1680
Glu Phe Gly Tyr Glu Glu Ser Met Val Met Val Gln Val Pro Trp Ser
545                 550                 555                 560 gca cca gag ggt ttg tct tct att aag tat ttg ttt tag agttatttaa       1729
Ala Pro Glu Gly Leu Ser Ser Ile Lys Tyr Leu Phe
                565                 570 ggtgcttaat tgaaaaaaaa aaaaaaaaaa aaa                                  1762

<210> SEQ ID NO 9
<211> LENGTH: 25
<212> TYPE: DNA
<213> ORGANISM: Artificial Sequence
<220> FEATURE:
```

-continued

<223> OTHER INFORMATION: Designed oligonucleotide primer to obtain
      raffinose synthase gene.

<400> SEQUENCE: 9
ccaatctgat catgcttgtg ccgaa                                              25

<210> SEQ ID NO 10
<211> LENGTH: 30
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 10
ggaacaaagt tatgcactat tatttaaggt                                         30

<210> SEQ ID NO 11
<211> LENGTH: 27
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 11
ctaccaaatt ccacaactta aagttca                                            27

<210> SEQ ID NO 12
<211> LENGTH: 32
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 12
ggaataataa gcttcacaca tactgtactc tc                                      32

<210> SEQ ID NO 13
<211> LENGTH: 30
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 13
atggctccaa gctttagcaa ggaaaattcc                                         30

<210> SEQ ID NO 14
<211> LENGTH: 30
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 14
tcaaaataag tactcaacag tggtaaaacc                                         30

<210> SEQ ID NO 15
<211> LENGTH: 30
<212> TYPE: DNA
<213> ORGANISM: Artificial Sequence
<220> FEATURE:
<223> OTHER INFORMATION: Designed oligonucleotide primer to obtain -continued raffinose synthase gene.

<400> SEQUENCE: 15
ttggaagaga agacgccgcc gggaatcgtc                    30

<210> SEQ ID NO 16
<211> LENGTH: 30
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 16
ttaagccccg gcgagagctc tggccggaca                    30

<210> SEQ ID NO 17
<211> LENGTH: 30
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 17
accaatccaa aatctcatca ataatcgca                     30

<210> SEQ ID NO 18
<211> LENGTH: 30
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 18
aaataatagg ggcagtacaa attacaccac                    30

<210> SEQ ID NO 19
<211> LENGTH: 29
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 19
atggctccac cgagcgtaat taaatccga                     29

<210> SEQ ID NO 20
<211> LENGTH: 30
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 20
ctaaaactca tacttaatag aagacaaacc                    30

<210> SEQ ID NO 21
<211> LENGTH: 41
<212> TYPE: DNA
<213> ORGANISM: Artificial Sequence
<220> FEATURE:
<223> OTHER INFORMATION: Designed oligonucleotide primer to obtain
      raffinose synthase gene,n is i.

<400> SEQUENCE: 21
cgatggatgg gnaanttnat ncanccngan tggganatgt t    41

<210> SEQ ID NO 22
<211> LENGTH: 32
<212> TYPE: DNA
<213> ORGANISM: Artificial Sequence
<220> FEATURE:
<223> OTHER INFORMATION: Designed oligonucleotide primer to obtain
      raffinose synthase gene, n is i, r is a or g.

<400> SEQUENCE: 22
ggccacatnt tnacnarncc natnggngcn aa    32

<210> SEQ ID NO 23
<211> LENGTH: 30
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 23
tgttactagg cgaaacaaga gtagctctga    30

<210> SEQ ID NO 24
<211> LENGTH: 47
<212> TYPE: DNA
<213> ORGANISM: Artificial Sequence
<220> FEATURE:
<223> OTHER INFORMATION: Designed oligonucleotide primer to obtain
      raffinose synthase gene, n is i.

<400> SEQUENCE: 24
cgaggnggnt gnccnccngg nttngtnatn atngangang gntggca    47

<210> SEQ ID NO 25
<211> LENGTH: 29
<212> TYPE: DNA
<213> ORGANISM: Artificial Sequence
<220> FEATURE:
<223> OTHER INFORMATION: Designed oligonucleotide primer to obtain
      raffinose synthase gene, n is i, y is t or c, r is a or g.

<400> SEQUENCE: 25
atyttrtcna cngcnarrtc ytccatngt    29

<210> SEQ ID NO 26
<211> LENGTH: 38
<212> TYPE: DNA
<213> ORGANISM: Artificial Sequence
<220> FEATURE:
<223> OTHER INFORMATION: Designed oligonucleotide primer to obtain
      raffinose synthase gene, n is i, y is t or c.

<400> SEQUENCE: 26
ggnacntant ggytncangg ntgncanatg gtncantg    38

<210> SEQ ID NO 27
<211> LENGTH: 32
<212> TYPE: DNA
<213> ORGANISM: Artificial Sequence
<220> FEATURE:
<223> OTHER INFORMATION: Designed oligonucleotide primer to obtain
      raffinose synthase gene, n is i, r is a or g.

```
<400> SEQUENCE: 27
ggccacatnt tnacnarncc natnggngcn aa                              32

<210> SEQ ID NO 28
<211> LENGTH: 26
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 28
atctatttgt catgacgatg atccga                                     26

<210> SEQ ID NO 29
<211> LENGTH: 30
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 29
ggccctcatt cccatattgg gatgatcctc                                 30

<210> SEQ ID NO 30
<211> LENGTH: 30
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 30
aagcatgcca acatacaca tgctcaacag                                  30

<210> SEQ ID NO 31
<211> LENGTH: 30
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 31
agacccgggg aaagctttgg ggttactact                                 30

<210> SEQ ID NO 32
<211> LENGTH: 28
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 32
tggatgggaa actttataca ccctgact                                   28

<210> SEQ ID NO 33
<211> LENGTH: 28
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 33
```

```
gacatgttcc catctacaca cccttgtg                                    28
```

```
<210> SEQ ID NO 34
<211> LENGTH: 30
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 34
```

```
ccaatttatg ttagtgatgt tgttggcaag                                  30
```

```
<210> SEQ ID NO 35
<211> LENGTH: 26
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 35
```

```
tcgactccca gggtagaatt gtcatc                                      26
```

```
<210> SEQ ID NO 36
<211> LENGTH: 35
<212> TYPE: DNA
<213> ORGANISM: Artificial Sequence
<220> FEATURE:
<223> OTHER INFORMATION: Designed oligonucleotide primer to obtain
      raffinose synthase gene, n is i.

<400> SEQUENCE: 36
```

```
cgattnaang tntggtggac nacncantgg gtngg                            35
```

```
<210> SEQ ID NO 37
<211> LENGTH: 38
<212> TYPE: DNA
<213> ORGANISM: Artificial Sequence
<220> FEATURE:
<223> OTHER INFORMATION: Designed oligonucleotide primer to obtain
      raffinose synthase gene, n is i, r is a or g.

<400> SEQUENCE: 37
```

```
cantgnacca tntgncancc ntgnarccan tangtncc                         38
```

```
<210> SEQ ID NO 38
<211> LENGTH: 30
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 38
```

```
gttagggttc atatgaacac cttcaagctc                                  30
```

```
<210> SEQ ID NO 39
<211> LENGTH: 26
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 39
```
caacggcgag atcttgcatc gtcaac    26

<210> SEQ ID NO 40
<211> LENGTH: 30
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 40
ggattcgaca caaaccgcca cgtcatcgtc    30

<210> SEQ ID NO 41
<211> LENGTH: 27
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 41
ccacgtgcac cacccgaact tatcgac    27

<210> SEQ ID NO 42
<211> LENGTH: 30
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 42
aacatcgata ccatcggagt catgtccaat    30

<210> SEQ ID NO 43
<211> LENGTH: 30
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 43
gttagggttc atatgaacac cttcaagctc    30

<210> SEQ ID NO 44
<211> LENGTH: 29
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 44
tctacgtctg gcacgcgctt tgcggctac    29

<210> SEQ ID NO 45
<211> LENGTH: 31
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 45
gttgacgtca tccacatatt ggagatgttg t    31

```
<210> SEQ ID NO 46
<211> LENGTH: 29
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 46
gttatcgcta gcatggagca ctgtaatga                                      29

<210> SEQ ID NO 47
<211> LENGTH: 35
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 47
aacgagctca atccaaaatc tcatcaaata atcgc                               35

<210> SEQ ID NO 48
<211> LENGTH: 25
<212> TYPE: DNA
<213> ORGANISM: Artificial Sequence
<220> FEATURE:
<223> OTHER INFORMATION: Designed oligonucleotide primer to obtain
      raffinose synthase gene.

<400> SEQUENCE: 48
acaatagttg agggcggaag agtag                                          25

<210> SEQ ID NO 49
<211> LENGTH: 25
<212> TYPE: DNA
<213> ORGANISM: Artificial Sequence
<220> FEATURE:
<223> OTHER INFORMATION: Designed oligonucleotide linker to obtain
      raffinose synthase gene.

<400> SEQUENCE: 49
gatcgagctc gtgtcggatc cagct                                          25

<210> SEQ ID NO 50
<211> LENGTH: 17
<212> TYPE: DNA
<213> ORGANISM: Artificial Sequence
<220> FEATURE:
<223> OTHER INFORMATION: Designed oligonucleotide linker to obtain
      raffinose synthase gene.

<400> SEQUENCE: 50
ggatccgaca cgagctc                                                   17

<210> SEQ ID NO 51
<211> LENGTH: 30
<212> TYPE: DNA
<213> ORGANISM: Artificial Sequence
<220> FEATURE:
<223> OTHER INFORMATION: Designed oligonucleotide primer to confirm
      direction of the inserted raffinose synthase gene.

<400> SEQUENCE: 51
cctcctcgga ttccattgcc cagctatctg                                     30
```

```
<210> SEQ ID NO 52
<211> LENGTH: 30
<212> TYPE: DNA
<213> ORGANISM: Artificial Sequence
<220> FEATURE:
<223> OTHER INFORMATION: Designed oligonucleotide primer to confirm
      direction of the inserted raffinose synthase gene.

<400> SEQUENCE: 52
ggattcgaca caaaccgcca cgtcatcgtc                                      30

<210> SEQ ID NO 53
<211> LENGTH: 29
<212> TYPE: DNA
<213> ORGANISM: Artificial Sequence
<220> FEATURE:
<223> OTHER INFORMATION: Designed oligonucleotide primer to confirm
      direction of the inserted raffinose synthase gene.

<400> SEQUENCE: 53
tctacgtctg gcacgcgctt tgcggctac                                       29
```